United States Patent
Southern et al.

(10) Patent No.: US 6,218,111 B1
(45) Date of Patent: *Apr. 17, 2001

(54) TAG REAGENT AND ASSAY METHOD

(75) Inventors: Edwin Southern, Oxford; William Jonathan Cummins, Tring, both of (GB)

(73) Assignee: Oxford Gene Technology Limited, Oxford (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/988,384

(22) Filed: Dec. 10, 1997

Related U.S. Application Data

(63) Continuation of application No. 08/586,875, filed as application No. PCT/GB94/01675 on Aug. 1, 1994, now Pat. No. 5,770,367.

(30) Foreign Application Priority Data

Jul. 30, 1993 (GB) .................................................. 9315847

(51) Int. Cl.[7] .............................. C12Q 1/68; C07H 19/00; C07H 21/00; C07H 21/02
(52) U.S. Cl. .............................. 435/6; 435/91.1; 435/912; 536/22.1; 536/23.1; 536/25.3; 536/25.31; 536/25.32
(58) Field of Search .............................. 435/6, 91.1, 91.2; 536/22.1, 23.1, 25.3, 25.31, 25.32

(56) References Cited

U.S. PATENT DOCUMENTS

| 5,003,059 | * | 3/1991 | Brennan | 536/27 |
| 5,258,506 |   | 11/1993 | Urdea et al. | 536/23.1 |

FOREIGN PATENT DOCUMENTS

| WO93/05183 | 3/1993 | (WO) . |
| WO93/06121 | 4/1993 | (WO) . |

OTHER PUBLICATIONS

S. Brenner et al., *Proc. Natl. Acad. Sci.*, 89(12), 5381–5383 (Jun. 15, 1992).

G.R. Parr et al., *Rapid Communication in Mass Spectrometry*, 6(6), 369–372 (Jun. 1992).

E. Nordhoff et al., *Nucl. Acids. Res.*, 21(15), 3347–3357 (Jul. 25, 1993).

* cited by examiner

*Primary Examiner*—Jezia Riley
(74) *Attorney, Agent, or Firm*—Wenderoth, Lind & Ponack, L.L.P.

(57) ABSTRACT

This invention provides reagents, libraries and sets of the reagents, and assay methods using the reagents, the reagents comprising an analyte moiety and a tag moiety, wherein the tag moiety contains information defining the identify and location of the analyte residues of the analyte moiety which is detectable by mass spectrometry.

56 Claims, 5 Drawing Sheets

GENERAL SCHEME FOR SYNTHESIS OF MOLECULES WITH SPECIFIC TAGS

GENERAL SCHEME FOR SYNTHESIS OF MOLECULES WITH SPECIFIC TAGS

THREE TYPES OF MOLECULE-SPECIFIC TAGS
POSITION- AND GROUP- SPECIFIC REPORTERS

GROUP-SPECIFIC REPORTERS-POSITIONS SPECIFIED BY PARTIAL PRODUCTS

GROUP-SPECIFIC END-LABELS-POSITIONS SPECIFIED BY PARTIAL PRODUCTS

SYNTHESIS OF CODED OLIGONUCLEOTIDES

```
                        SEQUENCE LISTING (1) GENERAL INFORMATION:

(iii) NUMBER OF SEQUENCES:  2

(2) INFORMATION FOR SEQ ID NO:1:

(i) SEQUENCE CHARACTERISTICS:
         (A) LENGTH:  21 base pairs
         (B) TYPE:  nucleic acid
         (C) STRANDEDNESS:  single
         (D) TOPOLOGY:  linear (xi) SEQUENCE DESCRIPTION: SEQ ID NO:1:

ATCAAGTCAG AAAAATATAT A                                                  21

(2) INFORMATION FOR SEQ ID NO:2:

(i) SEQUENCE CHARACTERISTICS:
         (A) LENGTH:  10 base pairs
         (B) TYPE:  nucleic acid
         (C) STRANDEDNESS:  single
         (D) TOPOLOGY:  linear (xi) SEQUENCE DESCRIPTION: SEQ ID NO:2:

CTGACTTGAT                                                               10
```

TAG REAGENT AND ASSAY METHOD

This is a continuation of U.S. Ser. No. 08/586,875, filed Feb. 5, 1996, now U.S. Pat. No. 5,770,367 which is a 371 of PCT/GB94/01675, filed Aug. 1, 1994.

In biological and chemical analyses, the use of analyte molecules labelled with reporter groups is routine. This invention addresses the idea of providing reagents having at least two analyte groups linked to one or more reporter groups. Such reagents can be used, in ways described below, to generate much more analytical information than can simple labelled analytes. It is possible to code reporter groups so that reagents carrying multiple analyte groups and multiple reporter groups can by synthesised combinatorially and used simultaneously and the reporter groups resolved in the analytical stage.

WO 93/06121 (Affymax) describes a synthetic oligomer library comprising a plurality of different members, each member comprising an oligomer composed of a sequence of monomers linked to one or more identifier tags identifying the sequence of monomers in the oligomer. The linkage between the oligomer and the identifier tag preferably comprises a solid particle. The identifier tag is preferably an oligonucleotide.

Proc. Natl. Acad. Sci., Vol 89, No. 12, Jun. 15, 1992, pages 5381–5383 (S Brenner and R A Lerner) describe encoded combinatorial chemistry for making a library of reagents each containing a genetic oligonucleotide tag.

In Rapid Communications in Mass Spectrometry, Vol 6, pages 369–372 (1992), G R Parr et al describe matrix-assisted laser desorption/ionisation mass spectrometry of synthetic oligodeoxyribonucleotides.

In Nucleic Acids Research, Vol 21, No. 15, Jul. 25, 1993, pages 3347–3357, E Nordhoff et al describe the ion stability of nucleic acids in infra-red matrix-assisted laser desorption/ionisation mass spectrometry.

In one aspect the present invention provides a reagent comprising
  a) an analyte moiety comprising at least two analyte residues, and linked to
  b) a tag moiety comprising one or more reporter groups suitable for detection by mass spectrometry, excluding oligonucleotides,
    wherein a reporter group designates an analyte residue, and the reporter group at each position of the tag moiety is chosen to designate an analyte residue at a defined position of the analyte moiety.

Preferably the analyte moiety is linked to the tag moiety by a link which is cleavable, e.g. photocleavable. There may be provided a linker group to which the analyte moiety and the tag moiety are both attached. Preferably the analyte moiety is a chain of n analyte residues, and the tag moiety is a chain of up to n reporter groups, the reporter group at each position of the tag chain being chosen to designate the analyte residue at a corresponding position of the analyte chain. n is an integer of at least 2, preferably 3 to 20.

The invention may be used for the detection of all analytes of interest. These include, but are not limited to, a protein/peptide chain so that the analyte residues are amino acid residues; a nucleic acid/oligonucleotide chain so that the analyte residues are nucleotide residues; a carbohydrate chain so that the analyte residues are sugar residues. Additionally the analyte may be a class of small molecules with biological, pharmacological or therapeutic activity. For example it could be a core molecule with the ability to vary various substituent groups eg. alkyl, esters, amines, ethers etc in a combinatorial manner with mass spectrometry tags.

The tag moiety and/or the or each reporter group in it is capable of being observed/detected/analysed so as to provide information about the nature of the analyte moiety, and/or the analyte residues in it.

In one embodiment, the reagent has the formula A—L—R where A is a chain of n analyte residues constituting the analyte moiety, L is the linker, R is a chain of up to n reporter groups constituting the tag moiety, and n is 2–20, wherein the tag moiety contains information defining the location of analyte residues in the analyte moiety.

The tag moiety consists of one or more reporter groups distinguishable by mass and thus capable of being analysed by mass spectrometry. The reporter groups may be chemically different and thus distinguished from one another by molecular weight. Or the reporter groups may be chemically identical, but distinguished from one another by containing different isotopes (e.g. $^{12}C/^{13}C$ and $^{1}H/^{2}H$ as discussed below). The tag moiety is, and/or the reporter groups are, suitable or adapted for analysis by mass spectrometry e.g. after cleavage by photochemical or other means from the reagent.

The advantages of mass spectrometry as a detection system are: its great sensitivity—only a few hundred molecules are needed to give a good signal; its wide dynamic range and high resolving power—molecules in the mass range 100 to 200,000 Daltons can be resolved with a resolution better than 0.01; its versatility—molecules of many different chemical structures are readily analysed; the potential to image analytes by combining mass spectrometry with, for example, scanning laser desorption: and the ability to make quantitative as opposed to merely qualitative measurements.

Thus mass-labelling combines advantages of radioactivity and fluorescence and has additional attributes which suggest novel applications.

In another aspect, the invention provides a library of the above reagents, wherein the library consists of a plurality of reagents each comprising a different analyte moiety of n analyte residues. For example, the library may consist of $4^n$ reagents each comprising a different oligonucleotide chain of n nucleotide residues. The reagents of the library may be present mixed together in solution.

In another aspect, the invention provides an assay method which comprises the steps of: providing a target substance; incubating the target substance with the said library of reagents under conditions to cause at least one reagent to bind to the target substance; removing non-bound reagents; recovering the tag moieties of the or each bound reagent; and analysing the recovered tag moieties as an indication of the nature of the analyte moieties bound to the target substance.

The target substance may be immobilised, as this provides a convenient means for separating bound from non-bound reagent. In one aspect, the target substance may be an organism or tissue or group of cells, and the assay may be performed to screen a family of candidate drugs. In another aspect, the target substance may be a nucleic acid, and this aspect is discussed in greater detail below.

Reference is directed to the accompanying drawings in which.

Figure 1:
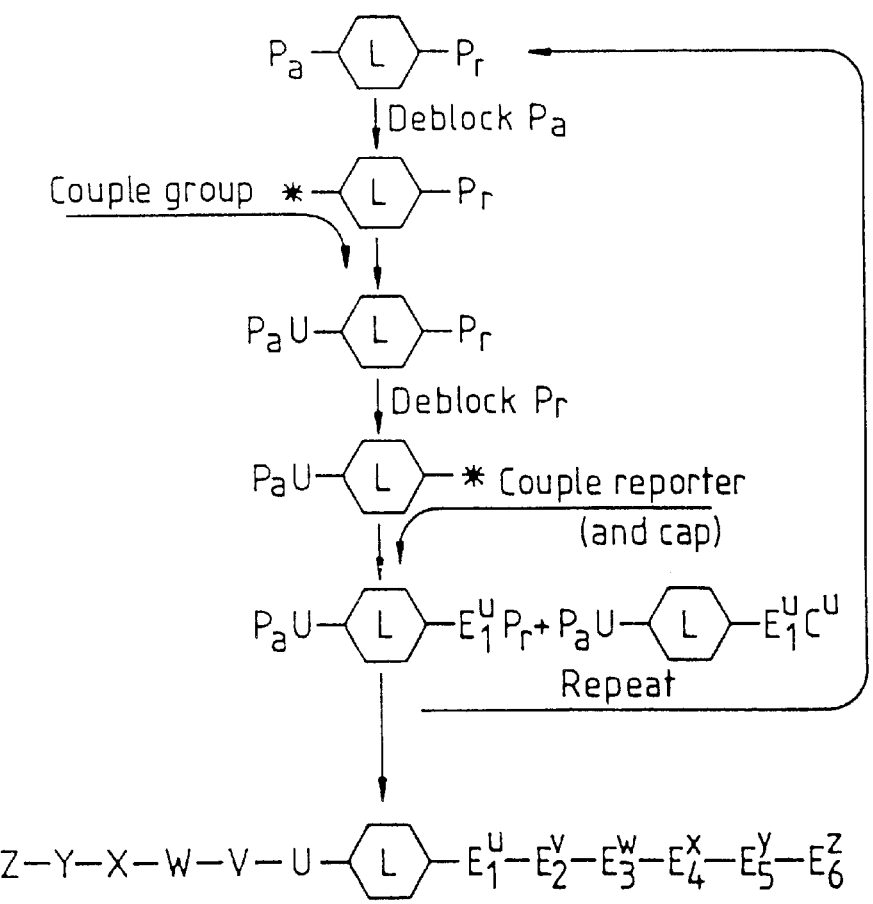
FIG. 1 is a general scheme for synthesis of reagents according to the invention.
Figure 2A:
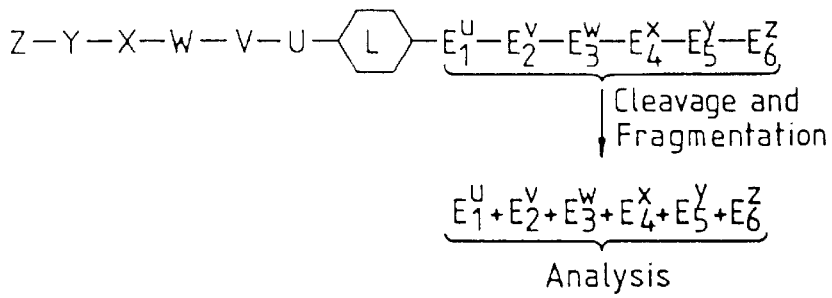
FIG. 2 shows reagents with three different systems of tag chains containing reporter groups.
Figure 2B:
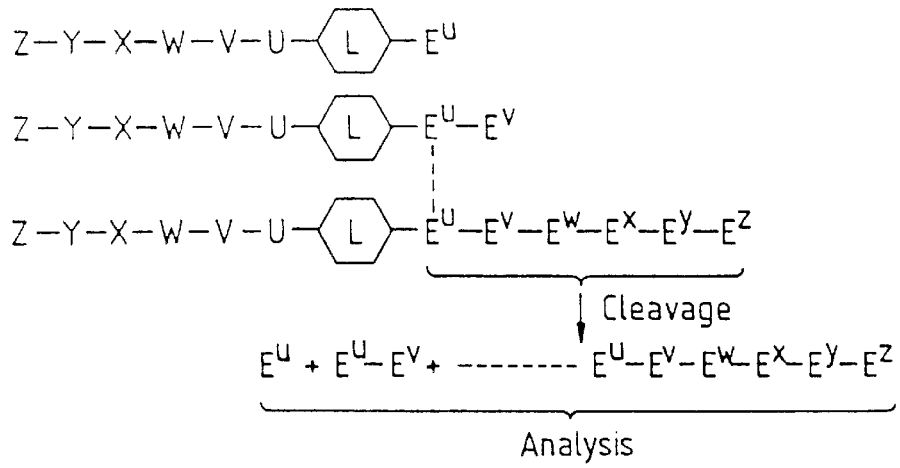
Figure 2C:
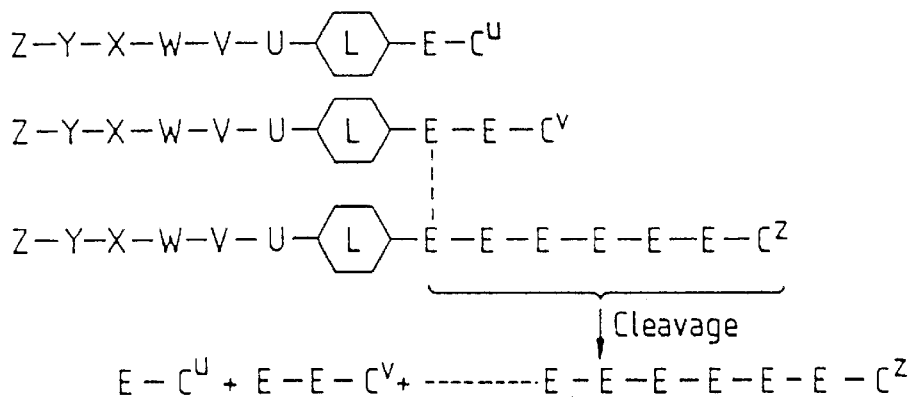

Legends to FIGS. 1 and 2 are included at the end of this specification.

Reference is directed to the example applications below, describing how the method may be applied to the analysis of nucleic acid sequences, and to screening candidate drugs.
Synthesis of Coded Taps.

The principle of the method used for tagging multiple analytes simultaneously is similar to that proposed by Brenner and Lerner (1992) for coding peptides with attached nucleic acid sequences. The intention of their idea is to add a tag which can be amplified by the polymerase chain reaction and read by sequencing the DNA molecule produced.

The structure of reagents is best illustrated by considering how they could be made. Synthesis starts with a bivalent or multivalent linker which can be extended stepwise in one direction to add a residue to the analyte and in another to add residue-specific reporter groups (FIG. 1). Suppose we wish to make a mixture of organic compounds, introducing different residues at each stage in the synthesis. For example, the mixture could comprise a set of peptides with different amino acid sequences or of oligonucleotides with different base sequences, or a set of variants with potential pharmacological activity with different groups attached to a core structure; in each case we wish to label each structural variant with a unique tag. This is done by dividing the synthesis at each step where different residues are added to the compound of interest, and adding corresponding residues to the tag.

Figure 3A:
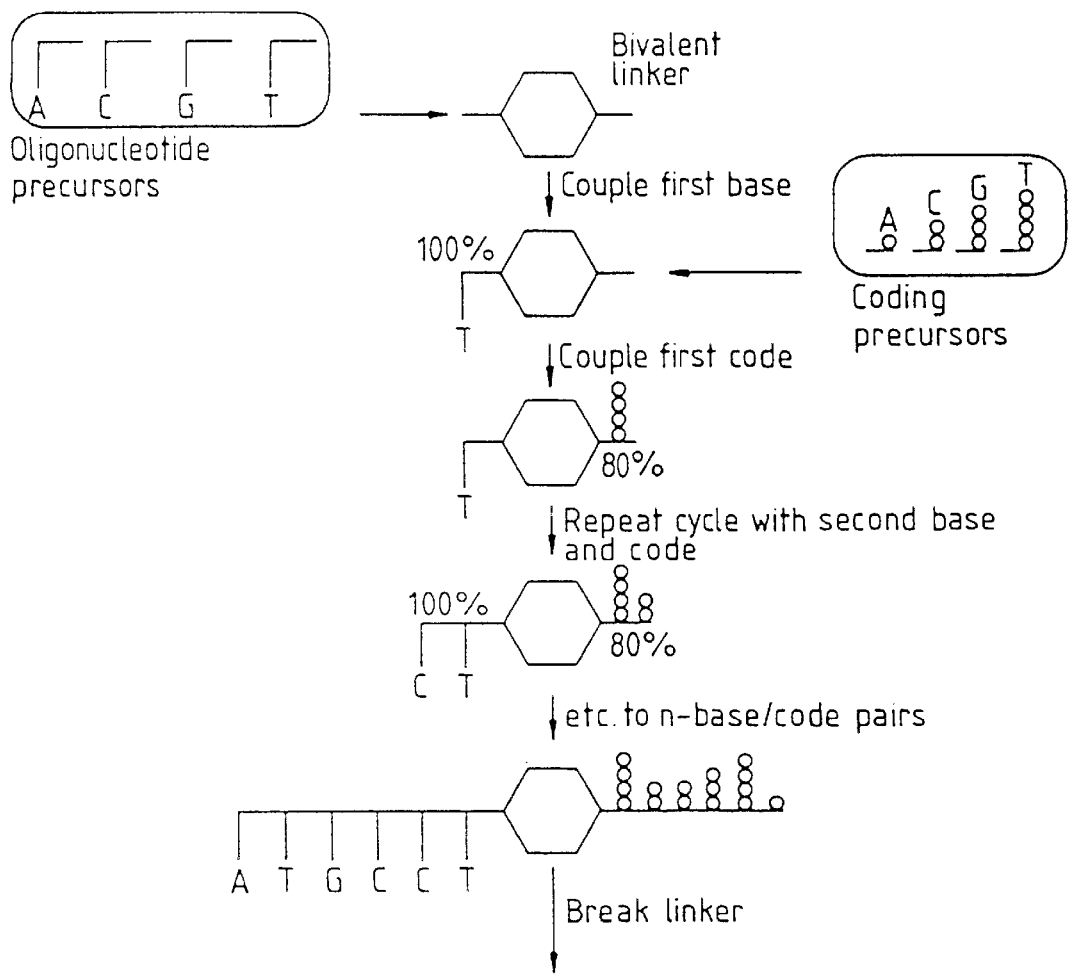
FIG. 3a is a diagram showing synthesis of coded oligonucleotides.

As an example, suppose we wish to make a mixture of 4096 hexanucleotides, each with a unique tag. Four samples of a bivalent linker would be coupled with each of the bases and with the unique reporter for the base (FIG. 3a). The four samples are then mixed, divided in four and the process repeated. The result is a set of dinucleotides each with a unique tag. The process is repeated until six coupling steps have been completed.
The Linker and Reporter Groups.

The linker should have one group that is compatible with analyte synthesis—hydroxyl, amino or sulphydryl group are all suitable for initiating oligonucleotide synthesis, and similar groups can be found to initiate other pathways, for example, synthesis of polypeptides. For some classes of compounds it may be desirable to start with a "core" compound which forms part of the analyte. The choice of the group(s) for starting addition of reporters depends on the nature of the reporter groups and the chemistry used to couple them. This chemistry has to be compatible with that used for synthesising the analyte. For the example of oligonucleotide synthesis, there are a number of alternatives. The established method uses benzoyl and isopropyl groups to protect the bases, acid-labile trityl groups for temporary protection of the 5'-OH groups during coupling, and β-cyanoethyl groups to protect the phosphates. The method used for coupling the reporters should not attack these protecting groups or other bonds in the oligonucleotide, and the synthesis of the tags should not be affected by the coupling, oxidation, and deprotection used in the extension of the oligonucleotide.

Figure 3B:
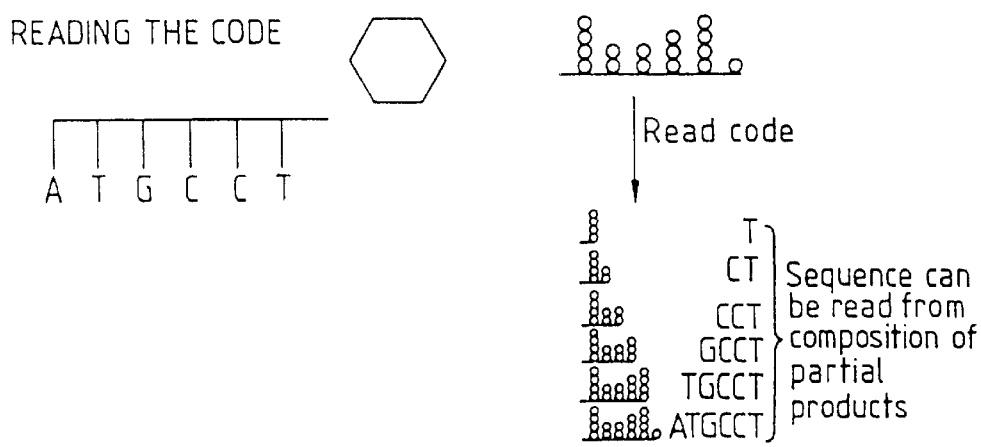
FIG. 3b is a diagram showing reading the code of a tag chain.

The coupling of the reporter monomers or the capping of the chain, may be incomplete at each step (FIGS. 2, B and C), so that the analyte is coupled to a nested set of reporter structures. This will make it easier to deduce the structure of the analyte from the composition of the tag (FIG. 1; FIG. 3). To make the synthesis easier it is desirable for the linker to be attached to a solid support by a linkage which can be cleaved without degrading the analyte or the reporter groups. Alternatively, the linker may carry a group such as a charged group or a lipophilic group which enables separation of intermediates and the final product from reagents.

The reporter groups could take many forms, the main consideration is the need to read the composition or sequence of the tag by mass spectrometry. Possibilities include groups with different atomic or formula weights, such as aliphatic chains of different lengths or different isotopic composition. Using isotopically labelled methylene groups, it is possible to assign a group of unique formula weight to each of four different reporters (Table 1).

TABLE 1

Example reporters based on isotopes of hydrogen and carbon:

| Isotopic Composition | Formula Weight (of —OCH$_2$) | Symbol | Base |
|---|---|---|---|
| $^{12}CH_2$ | 30 | $r_{30}$ | A |
| $^{12}CHD$, $^{13}CH_2$ | 31 | $r_{31}$ | C |
| $^{12}CD_2$, $^{13}CHD$ | 32 | $r_{32}$ | G |
| $^{13}CD_2$ | 33 | $r_{33}$ | T |

Taking the example of oligonucleotides these tags can make a set which allows the base at each position in the oligonucleotide to be read from the incremental masses of the partial products in the series (Table 2). All oligonucleotide sequences will give a unique series of tag fragment weights provided the smallest increment in adding a reporter is larger than the mass difference between the smallest and the largest reporter.

TABLE 2

Example of oligonucleotide with isotopic reporters:

G-A-T-C-T-A . . . P —$r_{30}$—$r_{33}$—$r_{31}$—$r_{33}$—$r_{30}$—$r_{32}$
Formula weights
of partial      $F_p$ + 30, + 63, + 94, + 127, + 157, + 190
products P = photolabile linker
$F_p$ = formula weight of P For mass spectrometry, it will be desirable to have a simple way of cleaving the tag chain from the analyte. There are several possibilities. Among methods compatible with oligonucleotide and peptide analytes are: light induced cleavage of a photolabile link; enzymatic cleavage, for example of an ester link; free-radical induced cleavage.

A further requirement is that the tags should be compatible with the chemical and biochemical processes used in the analysis: for the example of oligonucleotides used in molecular hybridisation or for one of the proposed sequencing methods, they must be soluble and they must not inhibit certain enzymatic reactions which may be used in the analysis. Experience has shown that oligoethylene glycol linkages, similar to the methylene analogues shown in Table 1, are compatible with molecular reassociation of oligonucleotides. Furthermore, such linkages are compatible with at least some enzymatic reactions as we have shown that oligonucleotides tethered to glass through a hexaethylene glycol linker can be converted to a 5'-phosphomonoester by treatment with polynucleotide kinase and ATP.
Desirable Properties of the Linker.

For the applications envisaged, it is desirable that the linker molecule has the following properties:

It should be possible to link it to a solid support to allow for synthetic cycles to produce the analyte and corresponding tags to proceed without the need for cumbersome purification of intermediates. Following synthesis cycles, the linker should be removable from the solid support under conditions which leave the analyte and tags intact. The functional group for tag synthesis should be such that it allows for the ready synthesis of tags which are distinguishable from each other by mass spectrometry.

The linker should have protected functional groups that allow for the extension of the analyte and the tags separately, under conditions in which the chemistry for one does not interfere with that of the other.

The linker should preferably carry a charged group so that mass spectrometry can be carried out in the absence of a matrix. Further to this aim, it is desirable that the tags should comprise compounds which are volatile enough to evaporate in the mass spectrometer, without recourse to complex techniques such as the electrospray. The tags should either produce stable ions or ions which fragment to characteristic patterns that can be used to identify the corresponding analyte.

The link between the tag and analyte should preferably be photocleavable, so that tags can be directly cleaved in the mass spectrometer by laser irradiation, and further cleavage to remove them completely to allow biochemical steps such as ligation, can be carried out conveniently by exposure to a lamp.

The linked products should preferably be soluble in aqueous solvents, so that they can be used in biochemical reactions.

The examples described herein show linkers with these desired properties.

Photocleavable Group.

The photocleavable group has been based on the known photolabile o-nitrobenzyl group. This group has been used as a protecting group for both the phosphate group and 2' hydroxy group in oligo nucleotide synthesis [see the review by Pillai Synthesis 1 (1980)]. In itself the o-nitrobenzyl group lacks further functionalisation for subsequent attachment of a linker between tags and analyte. Available from commercial sources is the compound 5-hydroxy-2-nitrobenzyl alcohol. It is known that OMe groups can be added in the 5,4 position without significant reduction in photolabile properties (see Pillai review). Thus, the 5-hydroxy-2-nitrobenzyl alcohol was used as a starting point with the aim of extending DNA synthesis from the benzyl alcohol and the linker chain to the tags from an ether coupling at the 5-hydroxy group.

The requirement is for a functional group to be present to permit the combinatorial synthesis of analytes and tags. A linker arm is therefore required from the photocleavable group to the required functional group for tag synthesis. It is also a preferment that the combinatorial synthesis be carried out on a solid support. Thus, the linker arm must be bivalent infunctional groups and have orthogonal protecting groups to permit selective synthetic transformation. Preferred tag reagents contain glycol linkages/ether linkages. For synthesis oligonucleotides are normally linked to a long chain amino CPG support via the 3' hydroxy and a succinic ester link. Thus the functional groups required were deemed to be alcohols.

The following intermediate compound has been synthesised.

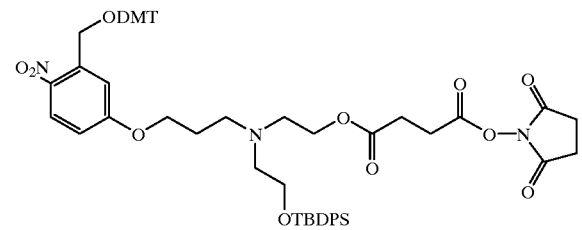

This comprises an aromatic linker carrying:
a methoxytrityl group (—CH$_2$ODMT) for analyte synthesis;
an o-nitro group for photocleavage;
an O-t-butyl diphenyl silyl group (OTBDPS) for tag synthesis;
a tertiary amine group for conversion to a positively charged group for analysis by mass spectrometry;
and an N-hydroxysuccinimidyl group for attachment to a support.

When the analyte is a peptide only minor modifications to conditions need be considered. The 2-nitrobenzyl group is stable under most of the conditions of peptide synthesis and it and related analogues have already been used as photo labile groups in peptide synthesis (see Pillai review and the references contained therein). There are already several resins suited to peptide synthesis with different modes of cleavage. The orthogonal protecting groups for analyte and tag synthesis would be based on t-butoxycarbonyl and 2-methoxyethoxymethyl. The t-butoxycarbonyl group would be used to protect the amino group in the amino acids with cleavage being effected by a trifluoroacetic acid treatment. The 2-methoxyethoxymethyl would be used to protect the tagging groups and the tags based on mass diffentiated on 1, n alkyldiol derivatives as before. The cleavage of t-butoxycarbonyl groups has been shown to be compatible with the 2-methoxyethoxymethyl protecting groups. The 2-methoxyethoxymethyl protecting groups can be selectively cleaved with zinc bromide in dichloromethane. While the above illustrates the procedure those skilled in the art will recognise that this set of orthogonal protecting groups is by no means limiting but serves as a representative example.

Detection and Analysis of Reporters.

Photocleavage is the favoured method of releasing tags from analytes; it is fast, can be carried out in the dry state, and scanning lasers can be used to image at a very small scale, small enough to image features within cells (de Vries et al., 1992), so that the proposed method could be used to detect the positions of specific analytes that had been used to "stain" the surface or the insides of cells, or different cells in a tissue slice, such as may be required to image interactions between ligands, e.g. candidate drugs, and their receptors.

Photosensitive protecting groups are available for a very wide range of chemical residues [reviewed in Pillai, 1980]. The photolabile o-nitro benzyl group which can be used as a protecting group for a wide range of compounds forms an ideal starting point for a linker for many analytes that could be envisaged, peptides and oligonucleotides among them. Taking the example of oligonucleotides, it provides a photosensitive link that can be broken quantitatively to give a hydroxyl group. This will permit the deprotected oligonucleotide to take place in the ligation extension as described in the sequencing method below. Furthermore, the group is known to be stable during oligonucleotide synthesis. It would be necessary to modify the benzyl ring to provide a group that can be used to initiate the synthesis of the tags; reporters such as the oligoethyleneglycol series described above do not interfere with the photochemical cleavage reaction of the o-nitrobenzoyl group (Pillai op, cit.). Other groups can be added to the aromatic ring which enhance the cleavage; such groups could be exploited to add a charged group(s) to simplify analysis in the mass spectrometer. Modern mass spectrometers are capable of measuring a few hundred molecules with a resolution better than one Dalton in a hundred, up to a total mass of 200 kD. A preferred photolabile linker may be represented thus; in which the positively charged group R may be directly attached to the aromatic ring or may be present in one of the linker arms:

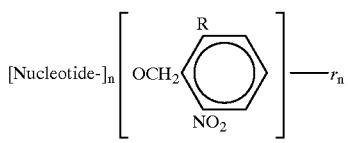

R = positively charged group

Instrumentation.

The proposed molecular tags would be analysed by one of several forms of mass spectrometry. For many purposes, although it will be desirable to cleave the tags from the analytes, it will not be necessary to fragment the tags, and indeed it may be undesirable as it could lead to ambiguities. Recent developments in mass spectrometry allow the measurement of very large molecules without too much fragmentation; and as it is possible to design the linker so that it is readily cleaved, under conditions where the rest of the tag is stable, fragmentation of the tag during measurement should be avoidable. The analyte group will, in most cases, be less volatile than the tag, and in many applications will be bound to a solid substrate, and thus prevented from interfering with mass spectrometry.

The linker illustrated above is very labile to photon irradiation under conditions which will cause no cleavage of the great majority of covalent chemical bonds. A suitable instrument has been described [de Vries et al., 1992]. This uses a laser that can be focussed down to a spot smaller than 1 $\mu$m. Images of up to 250 mm are scanned by moving a stage that can be positioned to 0.1 $\mu$m.

This instrument also allows for ionisation of the species to be measured by shining an ionising laser across the surface of the stage so that it interacts with the species lifted by the desorption laser. This could be useful for the present method if it were not possible to include a charged residue in the tags, or if fragmentation is desirable for reading the tags.

In another aspect the invention provides a method of sequencing a target nucleic acid, which method comprises the steps of:

a) providing an oligonucleotide immobilised on a support,
b) hybridising the target nucleic acid with the immobilised oligonucleotide,
c) incubating the hybrid from b) with the library as defined in which the reagents are mixed together in solution, so that an oligonucleotide chain of a first reagent of the library becomes hybridised to the target nucleic acid adjacent the immobilised oligonucleotide,
d) ligating the adjacent oligonucleotides, thus forming a ligated first reagent,
e) removing other non-ligated reagents, and
f) recovering and analysing the tag moiety of the ligated first reagent as an indication of the sequence of a first part of the target nucleic acid.

EXAMPLE APPLICATIONS

We illustrate potential applications by referring to ways in which coded oligonucleotides could be used in nucleic acid analysis.

Figure 4:
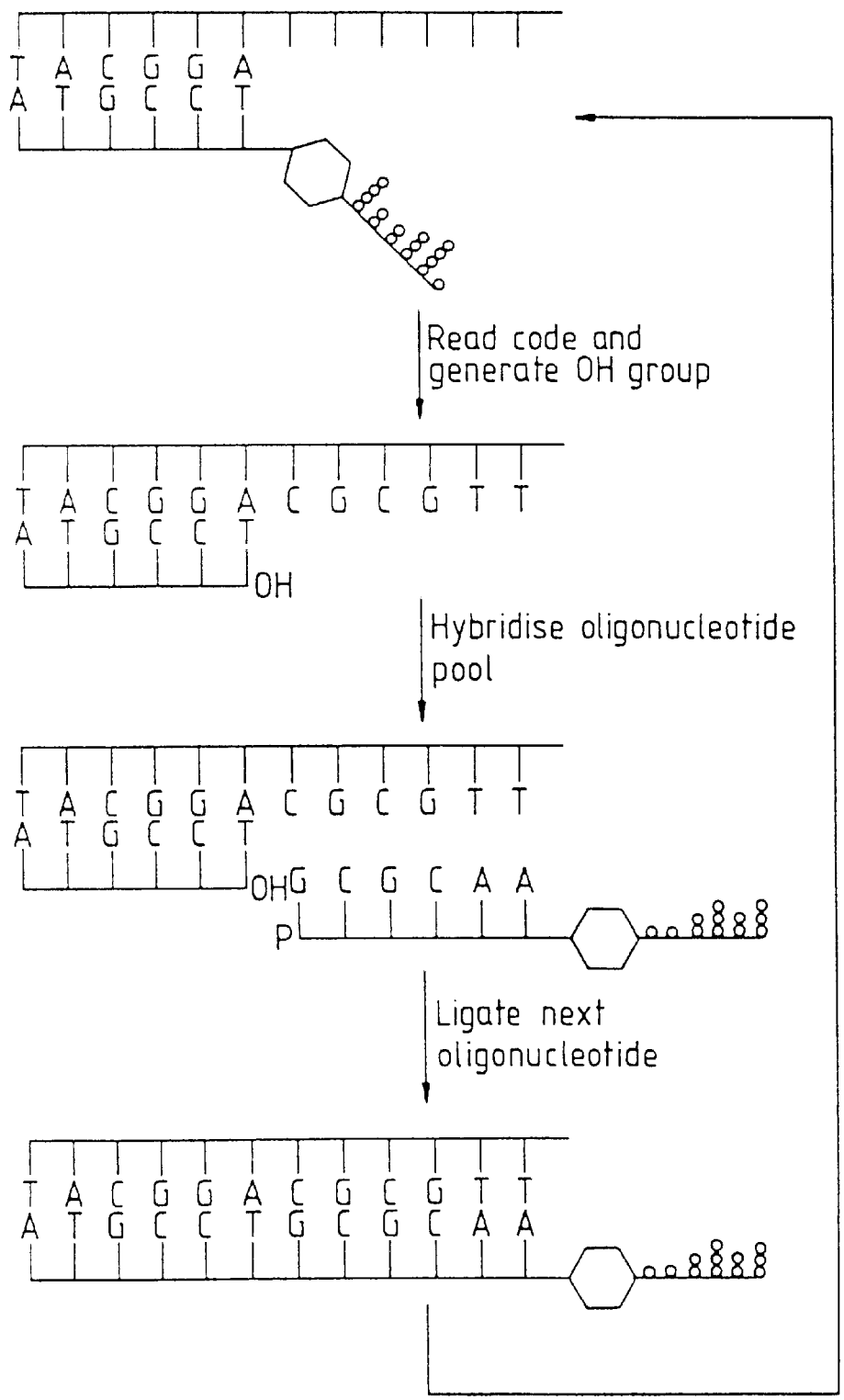
FIG. 4 is a diagram showing sequence analysis by progressive ligation.

1. Nucleic Acid Sequence Determination by Progressive Ligation (FIG. 4)

The sequence to be determined is first hybridised in step b) to an oligonucleotide attached to a solid support. If the DNA to be sequenced has been cloned in a single strand vector such as bacteriophage M 13, the "primer" oligonucleotide on the solid support can be chosen to be part of the vector sequence. In step c), the solid support carrying the hybrids from step b) is incubated with a solution of the coded oligonucleotide reagents, e.g. with the aforesaid library, comprising all sequences of a given length, say 4096 hexanucleotides ($4^n$ n-mers, in general). In step d), ligase is introduced so that the hexanucleotide complementary to the first six bases in the target DNA is joined to the immobilised primer oligonucleotide. By this step a first coded oligonucleotide reagent from the library is joined, by ligation of its oligonucleotide chain to the immobilised primer oligonucleotide, and is herein referred to as a ligated first reagent.

In step e), non-ligated reagents are removed, e.g. by washing. In step f), the linker of the ligated first reagent is broken to detach the tag chain, which is recovered and analysed as a indication of the sequence of a first part of the target DNA.

Preferably, removal of the linker also exposes a hydroxyl or phosphate group at the end of the first oligonucleotide chain, making it available for ligation with the oligonucleotide chain of a second reagent. Several methods for breaking the linker, including photochemical and enzymatic and chemical hydrolysis, can be used to generate the 3'-hydroxyl or 5'-phosphate group needed for further ligation. Steps c), d), e) and f) are then repeated. These steps involve hybridisation of a second reagent from the library, ligation recovery and analysis of the tag chain of the ligated second reagent, and generation of another 3'-hydroxyl or 5'-phosphate group needed for further ligation. The process can be repeated until the whole DNA sequence has been read or until yields in the reaction become too low to be useful.

Four stages of this sequence are shown diagrammatically in FIG. 4. The first diagram corresponds to the situation at the end of step e) first time round. The second diagram corresponds to the situation at the end of step f). The third diagram corresponds to the position at the end of step c) second time round. The fourth diagram corresponds to the situation at the end of step d) second time round. The cyclic nature of the technique is indicated.

2. Nucleic Acid Sequencing of Multiple Templates by Sequential Ligation

In an extension of the first example, it is envisaged that many sequences could be analysed simultaneously. For example, individual clones of the DNA to be sequenced could be immobilised:

a) Use can be made of an array of pins with the same vector oligonucleotide immobilised on the end of each. An individual clone of the target DNA is hybridised to the oligonucleotide immobilised on each individual pin. The array of pins carrying these hybrids is then incubated with the library of coded oligonucleotide reagents in a solution which also contains the ingredients for ligation. As a result of this step, each pin carries a different ligated reagent. Finally, the tag chain of each ligated reagent is recovered and analysed as before. If the pins of the array are suitably spaced, they may be dipped into the wells of microtitre plates, the first plate containing the templates to be sequenced, the second the library of reagents and ligation solution, and the third plate containing a reagent for cleaving the tag chains from the pins.

b) Alternatively, a surface may be coated with the primer oligonucleotide, preferably covalently attached through its 5' end or alternatively at some other point. Individual clones of the DNA to be sequenced are spotted at spaced locations on the coated support, so that each individual clone of the target DNA is hybridised to the oligonucleotide immobilised at an individual spaced location on the support. The support is then incubated with a solution containing the library of reagents and the ingredients for ligation. Non-ligated reagents are removed. Then the linker of the ligated reagent at each spaced location is cleaved and the tag recovered and analysed. Cleavage is preferably effected by a method such as laser desorption which can address small areas on the surface. An advantage of this approach is that very large numbers of DNA sequences can be analysed together.

3. Extension of Methods for Sequence Determination by Hybridisation to Oligonucleotides a) Format I.

Methods for spotting DNAs at high density on membranes are well established [Hoheisel et al., 1992; Ross et al., 1992]. For fingerprinting and for sequence determination, oligonucleotides must be applied either singly or in small sets so that the hybridisation patterns are not too complex to interpret; as a consequence, only a small proportion of templates give signal at each round of analysis. If the signal from each hybridisation contained coded information which allowed its sequence to be determined, more complex mixtures could be used and much more information collected at each round of hybridisation. The complexity of the mixture would depend on the length of the DNA templates and on the ability of the analytical method to resolve sequences in mixed oligonucleotides.

Nucleic acid probes encoded with these mass spectrometry tags or reporter groups will be very valuable where the use of multiple probes is advantageous eg. DNA fingerprinting or mutation analysis. The mass spectrometry tags offer the advantage of multiplexing.

A number of different probes each labelled with its own unique and appropriate mass spectrometry tag can be used together in typical nucleic acid hybridisation assays. The sequence of each individual probe which hybridises can be uniquely determined in the presence of others because of the separation and resolution of the tags in the mass spectrum.

In this aspect, the invention provides a method of sequencing a target nucleic acid, which method comprises the steps of:

i) providing the target nucleic acid immobilised on a support. Preferably individual clones of the target nucleic acid are immobilised at spaced locations on the support.

ii) incubating the immobilised target nucleic acid from I) with a plurality of the coded oligonucleotide reagents described above, so that the oligonucleotide chains of different reagents become hybridised to the target nucleic acid on the support, iii) removing non-hybridised reagents, and iv) recovering and analysing the tag moiety of each reagent as an indication of the sequence of a part of the target nucleic acid.

Preferably thereafter use is made of the library of reagents, with the hybridisation, ligation, cleavage and analysis steps being repeated cyclically to provide additional information about the sequence of the target nucleic acid.

b) Format II.

It is possible to determine nucleic acid sequences from the pattern of duplexes formed when they are hybridised to an array of oligonucleotides. The length of sequence that can be determined is approximately the square root of the size of the array: if an array of all 65,536 octanucleotides is used, the sequences to be determined should be around 200 bp [Southern et al., 1992]. The limit in size is imposed by the constraint that no run of eight bases should occur more than once in the sequence to be determined. The array and its use in sequence determination are described in International patent application WO 89/10977; and a method of providing an array of oligonucleotides immobilised e.g. by their 5'-ends or their 3'-ends on a surface is described in International application WO 90/03382.

By the method of the present invention, the sequence length that can be determined can be greatly extended. In this aspect of the invention, the method comprises the steps of:

a) Providing an array of oligonucleotides immobilised at spaced locations on a support, the oligonucleotide at one location being different from oligonucleotides at other locations. Preferably the sequence is known of the oligonucleotide immobilised by a covalent bond at each spaced location on the support, b) incubating the target nucleic acid with the array of immobilised oligonucleotides, so as to form hybrids at one or more spaced locations on the support, c) incubating the hybrids from b) with the library of coded oligonucleotide reagents, so that an oligonucleotide chain of a reagent of the library becomes hybridised to the target nucleic acid adjacent each immobilised oligonucleotide, d) ligating adjacent oligonucleotides thus forming ligated reagents at the one or more spaced locations on the support, e) removing other non-ligated reagents, and f) recovering and analysing the tag moiety of each ligated reagent as an indication of the sequence of a part of the target nucleic acid.

Preferably cleavage of the tag chain at each spaced location is effected photochemically by means of a laser. Preferably analysis of the tag chains is by mass spectrometry. Preferably the hybridisation, ligation, cleavage and analysis steps are repeated cyclically, as described above, so as to obtain additional information about the sequence of the target nucleic acid.

Figure 5:
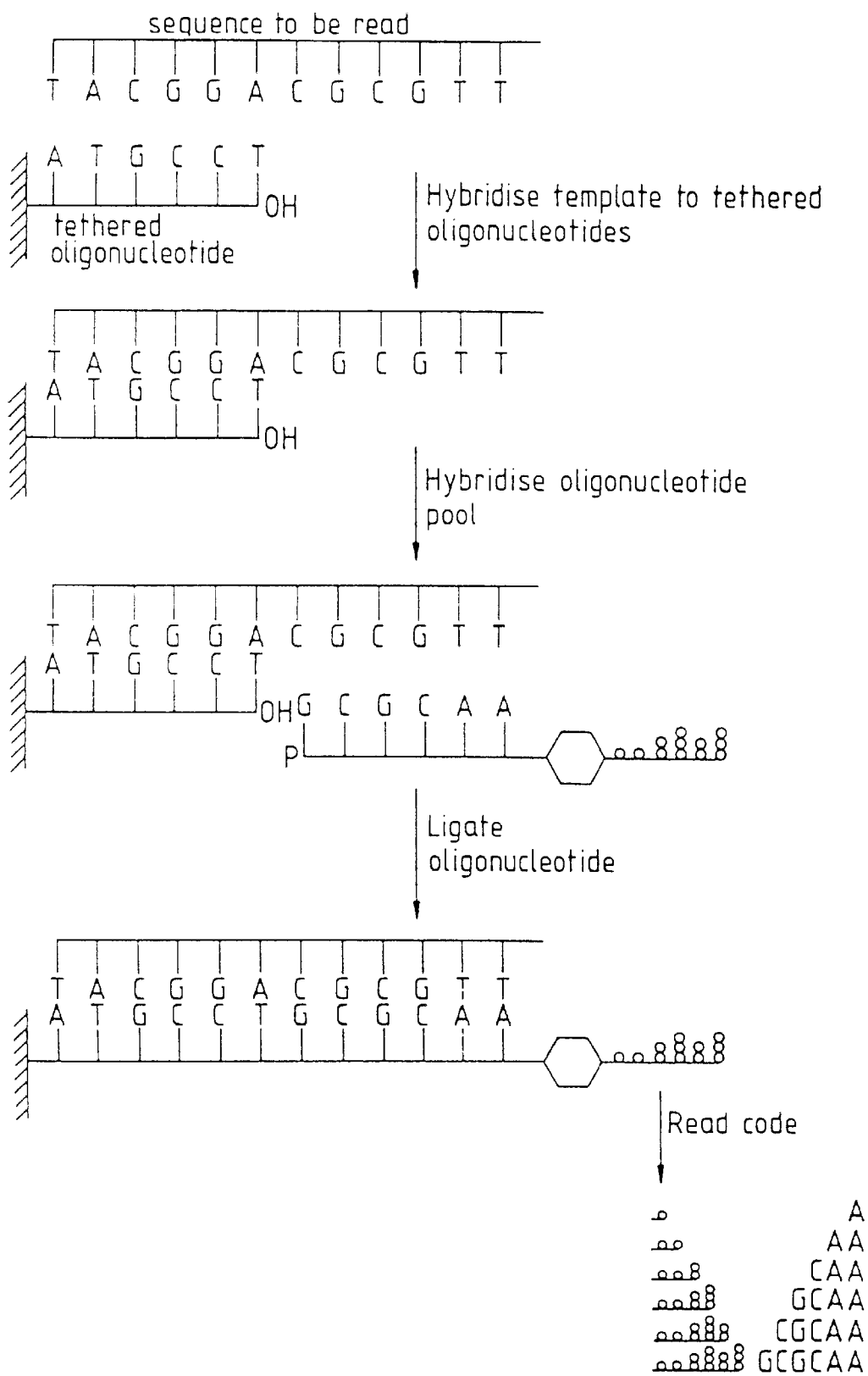
FIG. 5 is a diagram on extending the sequence read by hybridisation to an oligonucleotide assay.

A preferred sequence of operations is shown in the four diagrams constituting FIG. 5. The first diagram shows the position at the start of step b). The second diagram shows the position at the end of step b)—a portion of the target nucleic acid has become hybridised to a tethered oligonucleotide forming part of the array. The third diagram shows the position at the end of step c), and the fourth diagram shows the position at the end of step d); a reagent from the library has become hybridised to the target nucleic acid and ligated to the immobilised oligonucleotide.

The results of this extension of the known method are dramatic. A single extension by a length equal to the length of the oligonucleotides in the array squares the overall length that can be read, provided that the method used to read the tags can resolve mixtures. In this case the length that can be read from an array of octanucleotides extended by eight bases is around 60,000 bases.

Comparison of Hybridisation Analysis with Tagged Oligonucleotides With a) Gel-based Methods.

The most advanced instrument for automated sequence analysis is capable of reading around 40000 bases per day. This does not include the time for the biological and biochemical processes needed to provide the reactions that are loaded on the gel. If we assume that templates can be applied to a surface at a density of one per square millimeter [Hoheisel et al., 1992; Ross et al., 1992], 10000 could be applied to an area of 100×100 mm. After hybridisation, there would be several fmol of tagged oligonucleotide in each cell so a single 2 nsec pulse of the laser may release enough tag to read, but even if we assume that 100 pulses are needed, then the total time for a cell to be read is a few msec, so that all 10000 cells could be read in a few minutes. If the oligonucleotides were hexamers, the raw data acquired would be 60000 bases. For sequence determination, this would not be as informative as the equivalent raw data from a gel, because much longer continuous lengths are read from gels. This advantage for gels would, of course, be lost if the sequence read from the array could be extended by further rounds of analysis. But the fundamental advantage of array-based approaches is the parallelism which enables thousands of templates to be analysed together; the number that can be analysed on a gel is limited by the width of the gel to less than fifty.

b) Present Array-Based Methods.

The major drawbacks of existing array-based methods are:

a) The sequence that can be read from an array of size N is only $\approx\sqrt{N}$, so that most cells of the array are empty. By adding tagged oligonucleotides, the occupancy of the array could be near complete, so that information would be obtained from most cells. The reason for this is that additional information from the tags helps remove ambiguities due to multiple occurrences of short strings in the target sequence (Table 3).

b) The length of sequence that is read from each interaction with an oligonucleotide by hybridisation is necessarily limited to the length of the oligonucleotide. This causes problems including through repeating sequences, such as runs of a single base. Extending the read by ligation will permit reads as long as can be traversed by repeated ligations.

c) Of present detection methods, radioactivity has high sensitivity but poor resolution, fluorescence has low sensitivity and high resolution; both are relatively slow. The proposal to use mass spectrometry could improve resolution, speed and sensitivity, as well as adding the potential to read the sequences of tags.

TABLE 3

In general, the sequence that can be determined from templates distributed on a spatially segmented array is $\approx\sqrt{4^L} = 2^L$, where L is the sum of the continuous lengths read by oligonucleotides. This would include the length of the oligonucleotide on the solid support in example 3b but not in example 2.

| L | $2^L$ |
|---|---|
| 12 | 4096 |
| 14 | 16384 |
| 16 | 65536 |
| 18 | 2262144 |

Analytes with Potential Pharmacological Activity.

Many drugs are tissue-specific. Their action often depends on interaction with a cell-surface receptor. There are families of drugs based on core structures; for example, there are several comprising short peptides. It is useful to be able to trace candidate drugs to see which cells or tissues they may target. It would be useful to be able to trace many different candidates simultaneously. Using libraries of analytes tagged with coded mass-tags, it would be possible to trace interactions by examining cells or tissues in the mass spectrometer. If tags were attached by photolabile protecting groups, it would be possible to image whole animal or tissue sections using scanning laser cleavage, coupled with mass spectrometry.

The following Examples further illustrate the invention.

Examples 1 to 6 show steps, according to the following Reaction Scheme 1, in the synthesis of a compound (8) comprising an aromatic linker carrying: a methyloxytrityl group (—CH$_2$ODMT) for analyte synthesis; an o-nitro group for photocleavage; an o-t-butyl diphenyl silyl group (OTBDPS) for tag synthesis; a tertiary amino group for conversion to a positively charged group for analysis by mass spectrometry; and an N-hydroxysuccinimidyl group for attachment to a support.

Examples 7 and 8 show subsequent steps according to the following Reaction Scheme 2.

Examples 9 and 10 show steps, according to the following reaction Scheme 3, of preparing reporter groups (13) based on propan -1,3-diol.

Examples 11 to 13 show steps, according to the following Reaction Scheme 4, involved in attaching a protected propan -1,3-diol residue as a reporter group to compound (6).

Examples 14 to 19 describe the preparation, characterisation and use of various reagents according to the invention.

General Detail

5-Hydroxy-2-nitrobenzyl alcohol was purchased from Aldrich, long chain alkylamino controlled pore glass from Sigma. Anhydrous solvents refer to Aldrich Sure Seal grade material packed under Nitrogen. Triethylamine was predistilled from calcium hydride and stored under nitrogen prior to use. Other solvents and reagents are available from a range of commercial sources.

$^1$H NMRs were obtained on a Jeol 270 MHz machine using the solvent indicated and referenced to tetramethylsilane.

Infra Reds were obtained on a Nicolet 5DXC F.T. IR machine either as a potassium bromide disc or chloroform solution as indicated.

Medting points were obtained on a Gallenkamp melting point apparatus and are uncorrected.

Tlcs were run on Kieselgel 60F$_{254}$ aluminium backed Tlc plates using the solvent system indicated. The plates were visualised by both ultra violet and/or dipping in a 3% w/v ethanolic solution of molybdophosphoric acid and then heating with a hot air gun. Trityl containing species show up as a bright orange spot, alcohols as a blue spot.

Silica gel chromatography was performed using flash grade silica gel, particles size 40→63 μm.

Abbreviations used in the reaction schemes and text.
DMT—4,4'-dimethoxytrityl
THF—tetrahydrofuran
TBDPS—tert-butyidiphenylsilane
DMAD—4-dimethylaminopyridine
DCCI—dicyclohexyldicarbodiimide
CH$_2$Cl$_2$-dichloromethane
CPG—controlled pore glass
MeI—iodomethane
Tresyl—2,2,2-trifluoroethlsulphonyl

EXAMPLE 1

Synthesis of 5-hydroxy-O-(4,4'-dimethoxytrityl)-2-nitrobenzyl alcohol (Compound 2, Scheme 1)

To 5-hydroxy-2-nitrobenzyl alcohol (5.11 g, 30.2 mmol) dissolved in anhydrous pyridine (40 ml) was added 4,4'-dimethoxytrityl chloride (10.25 g, 30.2 mmol) and the flask stoppered. The reaction mixture was then left to stir at room temperture for a total of 72 hours. T.l.c. analysis (ether/pet, ether 40–60° C., 65%/35%) revealed the presence of a new trityl positive containing material with an R$_F$ of 0.27 and disappearance of the starting alcohol. The pyridine was then removed by rotary evaporation, with the last traces being removed by co-evaporation with toluene (x2). The resultant gum was dissolved up in ethyl acetate and the solution washed with water (x1) and brine (x1). The ethyl acetate solution was then dried over anhydrous magnesium sulphate and evaporated to a reddish brown gum. The gum was dissolved in CH$_2$Cl$_2$ (20 ml) and then applied to a silica gel column (14 cm×6.5 cm) which was eluated with ether/pet. ether 40–60° C., 65%/35%. The product fractions were combined and the solvent removed by rotary evaporation to give an off white solid (13.49 g, 95%, mpt. 80–82° C. with decomposition). An analytical sample was prepared by recrystallisation from chloroform/pet. ether 40–60° C., mpt. 134–7° C. with decomposition.

$^1$H NMR (270 MHz, CDCl$_3$δ): 3.79 (s, 6H, DMT-OC$\underline{H}_3$), 4.63 (s, 2H, C$\underline{H}_2$-ODMT), 6.77–6.85 (m, 5H, aryl), 7.22–7.49 (m, 9H, aryl), 7.63 (s, 1H aryl), 8.06 (d, 1H, J=9.06 Hz, aryl).

IR (KBr disc), 1610, 1509, 1447, 1334, 1248, 1090, 1060, 1033, 828 cm$^{-1}$.

EXAMPLE 2

Synthesis of O-(4,4'-dimethoxytrityl)-5-[1-(3-bromo-1-oxypropyl)]-2-nitrobenzylalcohol (Compound 3, Scheme 1)

To compound 2 (10.18 g, 21.6 mmol) dissolved in acetone (150 ml) was added 1,3-dibromopropane (11 mls, 108 mmol) and potassium carbonate (4.47 g, 32.3 mmol). The reaction mixture was then heated at 80° C. for a total of three hours and then stirred at room temperature for a further 16 hours. T.l.c. analysis (ether/pet. ether 40→60° C., 60%/40%) showed complete disappearance of the starting material and the formation of two new trityl containing species; R$_F$ 0.48 major, R$_F$ 0.23 minor. The acetone was then removed by rotary evaporation and the resultant residue partitioned between water and dichloromethane. The dichloromethane solution was separated and washed with brine. The dicholormethane solution was then dried over anhydrous magnesium sulphate and evaporated down to a gum. The gum was dissolved in dichloromethane 20 ml and then applied to a silica gel column (6.5 cm×14 cm) which was eluated with ether/pet. ether 40–60° C., 60%/40%. The pure product fractions were combined and the solvent removed by rotary evaporation to give compound 3 as a white solid (8.18 g, 64%, mpt. 132→4° C., R$_F$ 0.48 ether/pet ether 40–60° C., 60%/40%. A small sample was recrystallised from ethyl acetate/pet. ether for analytical purposes, mpt. 132–4° C.

$^1$H NMR: (270 MHz CDCl$_3$, δ): 2.40 (m, 2H, —CH$_2$—C$\underline{H}_2$—CH$_2$—), 3.64 (t, 2H, J=6.32 Hz, C$\underline{H}_2$Br), 3.79 (s, 6H, OC$\underline{H}_3$), 4.27 (t, 2H, J=6.04 Hz,—OCH$_2$CH$_2$), 4.66 (s,2H, Ar C$\underline{H}_2$ ODMT), 6.84 (d, 4H, J=8.79 Hz, DMT aryl), 7.20–7.50 (m, 10H,9 DMT aryl, 1 aryl) 7.68 (s, 1H, aryl), 8.1 (d,1H, J=9.06 Hz, aryl). IR (KBr disc) 1608, 1577, 1511, 1289, 1253, 1230, 1174, 1065, 1030 cm$^{-1}$.

EXAMPLE 3

Synthesis of N-[O-(tert-butyldiphenylsilyl)-2-oxyethyl)]-N-(2-hydroxyethyl) amine (Compound 5, Scheme 1)

To sodium hydride (0.76 g of a 60% dispersion in oil, 19 mmol) under N$_2$ was added anhydrous THF (15 ml)) followed by a slurry of diethanolamine (2 g, 19 mmol) in THF (30 ml) at such a rate as the evolution of hydrogen permitted. The reaction mixture was then stirred at room temperature for 30 minutes under N$_2$ during which time a grey precipitate formed. The generated alkoxide was quenched by the addition of tert-butylchlorodiphenylsilane (4.95 ml, 19 mmol) followed by stirring the reaction at room temperature for two hours under N$_2$, T.l.c. analysis (ethyl acetate) showed the generation of two new UV positive spots relative to starting material, major R$_F$ 0.05 minor R$_F$ 0.60. The THF was removed by rotary evaporation and the residue dissolved in a 0.1M sodium bicarbonate solution. The product was then extracted with ethyl acetate (x2). The ethyl acetate extracts were then combined and washed with brine (x1). The ethyl acetate solution was then dried over anhydrous magnesium sulphate and evaporated down to an oil. This oil was applied to a silica gel column which was elulated with a chloroform/methanol, 90%/10% Fractions with an R$_F$ of 0.33 were combined and rotary evaporated to give compound 5 as a white crystalline solid (3.93 g, 60%, mpt. 73→75° C.). A small sample was recrystallised from ethyl acetate/pet. ether 40–60° C. for analytical purposes, mpt. 76→77° C.

$^1$H NMR (270 MHz, CDCl$_3$, δ): 1.06 (s, 9H, 'Bu), 2.13 (brs, 1H, O$\underline{H}$,D$_2$O exchangable), 2.78 (m, 4H, C$\underline{H}_2$NHC$\underline{H}_2$), 3.63 (t, 2H, J=5.22 Hz, —CH$_2$OSi—), 3.78 (t,2H, J=5.22 Hz,C$\underline{H}_2$OH), 7.40 (m, 6H, aryl), 7.66 (m, 4H, aryl).

IR (KBr disc) 3100, 1430, 1114, 1080, 969, 749, 738, 707 cm$^{-1}$.

EXAMPLE 4

Synthesis of N-[O-(tert-butyldiphenylsilyl)-2-oxyethyl]-N-[O-(3(O-(4,4'-dimethoxytrityl)-1-oxymethyl)-4-nitrophenyl)-3-oxypropyl]-N-(2-hydroxyethyl)amine (Compound 6, Scheme 1)

To compound 3 (7.46 g, 12.6 mmol) dissolved in 1-methyl-2-pyrrolidinone (65 ml) was added compound 5

(8.63 g, 25.2 mmol). The reaction mixture was then heated at 80° C. for a total of 5 hours before being left to cool and stir at room temperature for a further 16 hours. T.l.c. analysis (ethyl acetate) showed the formation of a new trityl containing species, $R_F$ 0.51 and residual amounts of the two starting materials. The reaction mixed was poured into a mixture of water (600 ml) and brine (100 ml) and the product extracted with ethyl acetate (3×200 ml). The ethyl acetate extracts were then combined and dried over anhydrous magnesium sulphate. The ethyl acetate was then removed by rotary evaporation to give a brown gum from which a crystalline product slowly formed. The minimum amount of ethyl acetate was added to dissolve up the residual gum such that the crystalline product could be filtered, the hydrogen bromide salt of compound 5. The ethyl acetate solution was then applied to a silica gel column (13 cm×6.5 cm) which was eluted with ethyl acetate. Insufficient separation of residual compound 3 and the desired product was obtained from this column so the product fractions were combined and evaporated to a gum. This gum was dissolved up in the minimum of ethyl acetate necessary and applied to another silica gel column (14 cm×6.5 cm) eluting using a gradient eluation, first ethyl acetate/pet. ether 40→60° C., 50%/50% followed by ethyl acetate. The product fractions were combined and the solvent removed by rotary evaporation to give compound 6 as a gum. The last traces of solvent were removed by placing the gum under high vacuum for one hour. The yield of product was 7.64 g, 71%.

$^1$H NMR (270 MHz, CDCl$_3$, δ): 1.04 (s, 9H, 'Bu), 1.97 (m, 2H, —CH$_2$CH$_2$CH$_2$—), 2.7 (m, 6H, NCH$_2$), 3.56 (m, 2H, CH$_2$OH), 3.75 (m, 2H, CH$_2$OSi), 3.78 (s, 6H, DMT-OCH$_3$), 4.12 (m,2H, ArOCH$_2$CH$_2$), 4.64 (s, 2H, ArCH$_2$ODMT), 6.74–6.85 (m,5H,aryl) 7.2–7.65 (m, 20H, aryl), 8.05 (d,1H, aryl).

IR (KBr disc), 1608, 1579, 1509, 1287, 1251, 1232, 1112, 1092, 1064, 1035, 826, 754, 703, 613 cm$^{-1}$.

EXAMPLE 5

Synthesis of N-[O-(tert-butyldiphenylsilyl)-2-oxyethyl]-N-[O-(3(O-(4,4'-dimethoxytrityl)-1-oxymethyl)-4-nitrophenyl)-3-oxypropyl]-N-[O-(3-carboxylatopropionyl))-2-oxyethyl] amine (Compound 7, Scheme 1)

To compound 6 (5.64 g, 6.59 mmol) dissolved in anhydrous dichloromethane (40 ml) and anhydrous pyridine (50 ml) was added succinic anhydride (2.06 g 20.6 mmol) and. dimethylaminopyridine (210 mg, 1.72 mmol) and the flask stoppered. The reaction was then stirred at room temperature for a total of 72 hours. T.l.c. analysis (methanol/ethyl acetate, 10%/90%) showed the formation of a new trityl containing species, $R_F$ 0.45 and the disappearance of the starting material. The solvent was removed by rotary evaporation with the last traces of pyridine being removed by co-evaporation with toluene (x2). The resultant gum was then partitioned between chloroform and water. The organic phase was separated and the aqueous phase further extracted with chloroform (x1). The organic phases were then combined and washed with brine (x1). The chloroform solution was then dried with anhydrous magnesium sulphate and evaporated to a gum. The last traces of solvent were then removed by placing the gum under high vacuum for one hour to give compound 7, 6.75 g. This product was used in the next step without further purification.

$^1$H NMR (270 MHz, CDCl$_3$, δ): 1.0 (s, 9H, 'Bu), 1.9 (m, 2H, CH$_2$CH$_2$CH$_2$), 2.5 (m, 4H, COCH$_2$CH$_2$COOH), 2.7 (m, 6H, N-CH$_2$), 3.7 (m, 2H, CH$_2$OSi), 3.75 (s, 6H, DMT-OCH$_3$), 4.1 (m, 4H, CH$_2$OCO and Ar-OCH$_2$CH$_2$, 5.6 (s, 2H, ARCH$_2$ODMT), 6.7 (d, 1H, aryl), 6.8 (d,4H, aryl) 7.2→7.7 (m, 20H, aryl), 8.02 (d, 1H, aryl).

IR (CHCl$_3$ solution) 1736, 1608, 1579, 1509, 1288, 1251, 1232, 1175, 1158, 1112, 1093, 1065, 1035, 755, 703 cm$^{-1}$.

EXAMPLE 6

Synthesis of N-[O-tert-butyldiphenylsilyl)-2-oxyethyl]-N-[O-(3-(O-(4,4dimethoxytrityl)-1-oxymethyl)-4-nitrophenyl)-3-oxypropyl]-N-[(O-(succinyl(3-carboxylatopropionyl)))-2-oxyethyl] amine (Compound 8, Scheme 1)

To compound 7 (2.99 g, 3.13 mmol) dissolved in anhydrous dichloromethane (30 ml) was added dicyclohexylcarbodiimide (0.710 g, 3.45 mmol) and N-hydroxy succinimide (0.396 g, 3.44 mmol) and the flask stoppered. The reaction mixture was then allowed to stir at room temperature for 18 hours during which time a white precipitate formed. The white precipitate was filtered off and the dichloromethane solution washed with water (x1) and brine (x1). The dichloromethane solution was then dried over anhydrous magnesium sulphate and the solvent rotary evaporated off to give a foam, 3.26 g (99%). T.l.c. analysis (ethyl acetate) showed only one trityl containing species, $R_F$ 0.74 and no significant containment. Attempts to provide an analytical sample by passing a small amount of material down a silica gel column resulted in the decomposition of the active ester back to the acid (Compound 7). The material was therefore used in all further equipments without further purification.

$^1$H NMR (270 MHz, CDCl$_3$, δ): 1.04 (s, 9H, 'Bu), 1.97 (m, 2H, CH$_2$CH$_2$CH$_2$), 2.50→2.75 (m, 6H, succinyl CH$_2$+—OCCH$_2$), 2.76–2.86 (m, 6H, NCH$_2$), 3.08 (m, 2H, CH$_2$CO$_2$succinyl), 3.77 (s, 6H, DMTOCH$_3$), 3.86 (m, 2H, CH$_2$OSi), 4.1→4.2 (m, 4H, ArOCH$_2$+CH$_2$O$_2$C), 4.63 (s, 2H, ArCH$_2$ODMT, 6.7→6.9 (m, 5H, aryl), 7.01→7.7 (m, 20H, aryl) 8.05 (d, 1H, aryl).

IR (Br disc), 1742, 1713, 1509, 1288, 1251, 1211, 1175, 1090, 1067cm$^{-1}$.

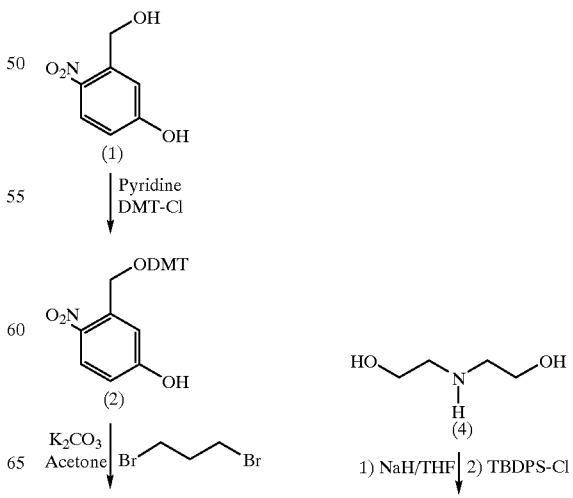

SCHEME 1

17

-continued

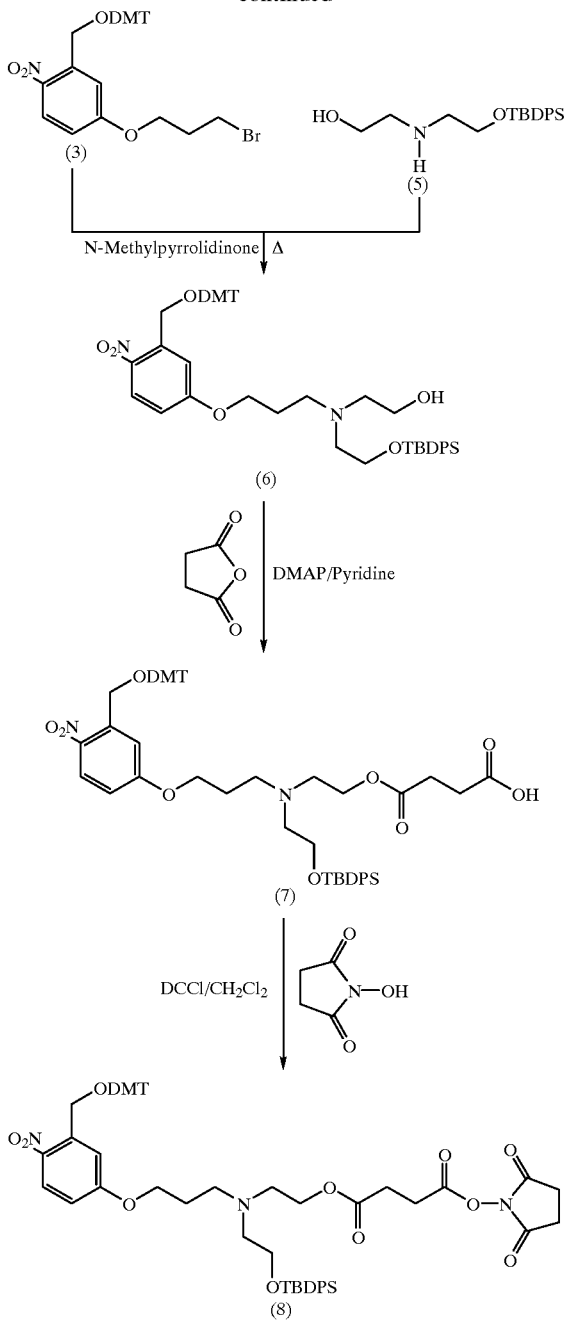

EXAMPLE 7

Derivatised Long Chain Alkylamino Controlled Pore Glass (Compound 9, Scheme 2)

Long chain alkylamino controlled pore glass (Sigma Chemical Co, 3.5 g) was pre-treated with trichloroacetic acid (1.5 g) dissolved in dichloromethane (50 ml) for 2½ hours, washed with aliquots of dichloromethane (100 ml total) and anhydrous ether (100 ml total) and dried in vacuo. To the CPG support was then added anhydrous pyridine (35 ml), dimethylaminopyridine (42 mg, 344 μmol), triethylamine (280 μl, 201 mmol) and compound (8) (see scheme 1) (736 mg, 700 μmol). The mixture was then gently agitated for a total of 18 hours after which time the beads were given

18 multiple washes of pyridine (7×10 ml), methanol (5×15 ml) and chloroform (5×15 ml) and then dried in vacuo.

EXAMPLE 8

Methylation of the Tertiary Amino Groups Attached to the CPG Support (Compound 10, Scheme 2)

To the derivatised long chain alkylamino controlled pore glass (Compound 9, Scheme 2) (1.0 g) was added anhydrous THF (10 ml) and iodomethane (0.5 ml, 8 mmol). The mixture was then gently agitated for a total of 18 hours after which time the beads were given multiple washes of anhydrous THF (5×10 ml) and then dried in vacuo.

SCHEME 2

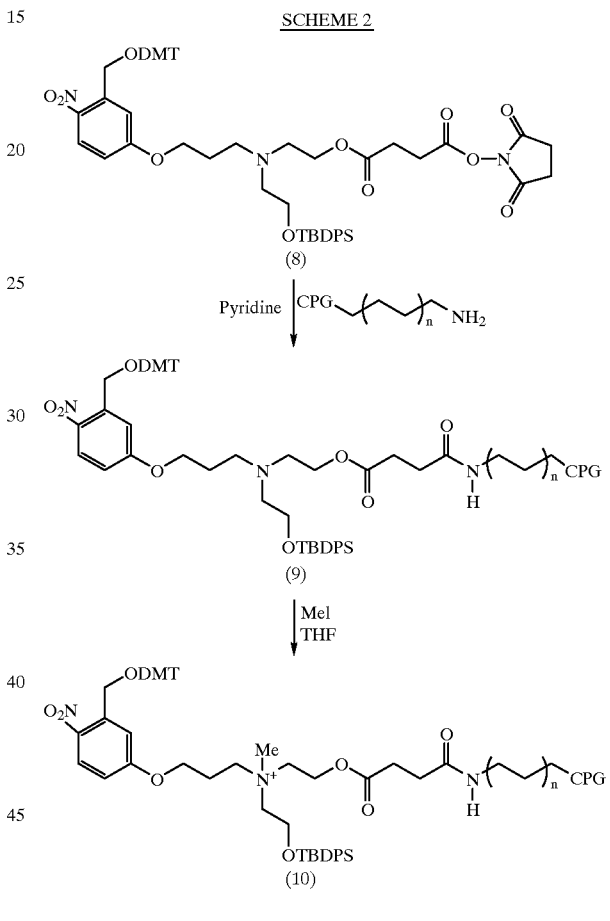

EXAMPLE 9

Synthesis of Mono Protected 1,3-propanediol Derivatives (Compounds 12a and 12b, Scheme 3)—general procedure To sodium hydride (1.05 g of a 60% dispersion in oil, 26.3 mmol) under $N_2$ was added anhydrous THF (10 ml) followed by dropwise addition of the 1,3-propanediol derivative (26.3 mmol) dissolved in anhydrous THF (20 ml). Stirring for an additional 30 minutes under $N_2$ ensured alkoxide formation as noted by the formation of a grey precipitate. The generated alkoxide was quenched by the dropwise addition of tert-butylchlorodiphenylisilane (7.24 g, 26.3 mmol) dissolved in anhydrous THF (20 ml) followed by stirring of the reaction under $N_2$ for a further 40 minutes. The THF was then removed by rotary evaporation and the residue partitioned between dichloromethane and 0.1M sodium bicarbonate solution. The dichloromethane solution was separated off and washed with brine (x1). The dichloromethane solution was then dried over magnesium sulphate and evaporated down to an oil. This oil was applied to a silica gel column (16 cm×5 cm) which was eluted with an ether/pet. ether 40→60° C., 30%/70% mixture. The product fractions were combined and rotary evaporated down to provide the desired 1,3-propanediol derivative.

For individual details of the compounds see below.

12a 1-O-tert-butyldiphenysilyl-1,3-propanediol, white crystalline solid, $R_F$ 0.21 ether/pet. ether 40→60° C., 30%/70%, 7.61 g, 92%, mpt. 40→42° C.

IR (KBr disc) 3400, 1448, 1112, 822, 734, 702, 689, 506, 488 cm$^{-1}$.

$^1$H NMR (270 MHz, CDCl$_3$, δ): 1.06 (s, 9H, 'Bu), 1.80 (m,2H, CH$_2$CH$_2$CH$_2$), 2.45 (t, 1H, OH), 3.84 (m, 4H,OC H$_2$CH$_2$CH$_2$O—), 7.40 (m, 6H, aryl), 7.68 (m,4H, aryl).

12b 2-methyl-1-O-tert-butyldiphenylsilyl-1,3-propanediol. Colourless oil, $R_F$ 0.21 ether/pet. ether 40→60° C., 30%/70%, 6.60 g, 77%.

IR (thin film) 3400, 1472, 1428, 1087, 1040, 823, 740, 702 cm$^{-1}$.

$^1$H NMR (270 MHz, CDCl$_3$, δ): 0.82 (d, 3H, J=6.87 Hz, CH$_3$), 1.06 (s,9H, 'Bu), 2.0 (m, 1H, CH—CH$_3$), 2.68 (t, 1H, OH), 3.64 (m, 4H, CH$_2$CH(CH$_3$), CH$_2$), 7.40 (m,6H, aryl), 7.68 (m, 4H, aryl).

See P G McDougal el al JOC, 51, 3388 (1986) for general procedures for the monosilylation of symmetric 1,n-diols.

EXAMPLE 10

Synthesis of the Treslate Derivatives (Compounds 13a and 13b, Scheme 3)-general Procedures To the alcohol derivative (4.94 mmol) dissolved in anhydrous dichloromethane (10 ml) and dry triethylamine (0.84 ml 6.03 mmol) under N$_2$ and cooled to between −15°→30° C. was added the tresylchloride (1 g, 5.48 mmol) in anhydrous dichloromethane (5 ml) dropwise over a 20→40 minutes. Stirring for an additional 30 minutes under N$_2$ at −15°→30° C. completed the reaction. The reaction mixture was then transferred to a separatory funnel and washed with ice cooled 1.0M hydrochloric acid (x1), ice cooled water (x1) and ice cooled brine (x1). The dichloromethane solution was then dried over magnesium sulphate and the solvent rotary evaporated off to give the treslate. The treslates were stored at −20° C. under N$_2$ until required.

For individual details of the compounds see below.

13a 1-O-tert-butyldiphenylsilyl-3-O-tresyl-1,3-propanediol. White crystalline solid, 1.74 g, 77% mpt. 34→35° C. Three ml of this reaction mixture was removed prior to work up of the reaction for addition to other reactions.

$^1$H NMR (270 MHz, CDCl$_3$, δ): 1.06 (s, 9H, 'Bu), 1.97, (m, 2H, CH$_2$CH$_2$CH$_2$), 3.77 (t, 2H, J=5.49 Hz, C H$_2$—O)—Si), 3.84 (q, 2H, J=8.79 Hz, CF$_3$—CH$_2$—O), 4.54 (t, 2H, J=6.05 Hz, Tresyl O-CH$_2$), 7.42 (m, 6H, aryl), 7.64 (m, 4H, aryl).

IR (KBr disc) 1386, 1329, 1274, 1258, 1185, 1164, 1137, 1094, 941, 763, 506 cm$^{-1}$.

13b 2-methyl-1-O-tert-butyldiphenylsilyl-3-O-tresyl-1,3-propanediol. Colourless oil, 2.57 g, 99%.

$^1$H NMR (270 MHz, CDCl$_3$, δ): 0.97 (d, 3H, J=6.87 Hz, CH$_3$), 1.06 (s, 9H, 'Bu), 2.10 (m, 1H, CHCH$_3$), 3.6 (m, 2H, CH$_2$OSi), 3.8 (q, 2H, J=8.79 Hz, CF$_3$CH$_2$), 4.40 (m, 2H, Tresyl-O-CH$_2$), 7.40 (m, 6H, aryl), 7.64 (m, 4H, aryl).

For general details of Treslates see R K Crossland et al JACS, 93, 4217 (1971).

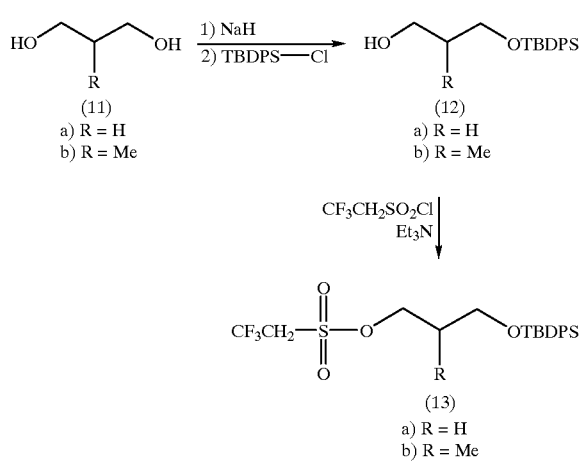

SCHEME 3

(11)
a) R = H
b) R = Me

(12)
a) R = H
b) R = Me

(13)
a) R = H
b) R = Me

EXAMPLE 11

Synthesis of N-[acetoxy-2-oxyethyl]-N-[O-(3(O-(4,4'-dimethoxytrityl)-1-oxymethyl)-4-nitrophenyl)-3-oxypropyl]-N-2-hydroxyethyl] amine (Compound 15, Scheme 4)

To compound 11 (1.72 g, 1.92 mmol) dissolved in anhydrous THF (20 ml) was added tetrabutylammonium fluoride (0.55 ml of a 1M solution in THF, 1.92 mmol). The reaction was then stirred for a total of two hours at room temperature. The reaction mixture was then diluted with water (50 ml) and the THF removed by rotary evaporation. The aqueous solution was then extracted with chloroform (x1). The organic solution was dried over anhydrous sodium sulphate and evaporated down to a gum. The product was purified by silica gel chromatography eluting the column with ethyl acetate. Product fractions were combined and rotary evaporated down to give compound 12 as a colourless gum which slowly crystallised on standing; 0.73 g, 58%, mpt. 95→97° C., $R_F$ 0.26 ethyl acetate.

$^1$H NMR (270 MHz, CDCl$_3$, δ): 1.75 (brs, 1H, OH), 2.0→2.1 (m, 5H, O$_2$CCH$_3$+CH$_2$CH$_2$CH$_2$), 2.70→2.81 (m, 6H, CH$_2$N), 3.58 (m, 2H, CH$_2$OSi), 3.79 (s, 6H, DMT-OC H$_3$), 4.17 (m, 4H, CH$_2$O), 4.64 (s, 2H, ArCH$_2$ODMT), 6.83 (d, 4H, DMT-aryl) 7.2→7.5 (m, 10H, aryl), 7.69 (s, 1H, aryl), 8.10 (d, 1H, aryl).

IR (KBr disc), 3459, 1738, 1608, 1577,1506, 1444, 1313, 1288, 1250, 1230, 1175, 1154, 1070, 1035, 984 cm$^{-1}$.

EXAMPLE 12

Synthesis or N-[O-(tert-butyldiphenylsilyl)-2-oxyethyl]-N-[O-(3(O-(4,4'-dimethoxytrityl)-1-oxymethyl)-4-nitrophenyl)-3-oxypropyl]-N-[acetoxy-2-oxyethyl] amine (Compound 14, Scheme 4)

To compound 6 (1.73 g, 2.02 mmol) dissolved in anhydrous pyridine (10 ml) was added acetic anhydride (0.5 ml, 4.54 mmol) and 4-dimethylaminopyridine (55 mg, 0.45 mmol) and the flask stoppered. The reaction mixture was then stirred at room temperature for a total of 16 hours after which time t.l.c. analysis (methanol/ethyl acetate 5%/95%)

showed the complete disappearance of the starting material and the formation of a new trityl containing spot, $R_F$ 0.80. The pyridine was removed by rotary evaporation with the last traces being removed with co-evaporation with toluene (x2). The resultant gum was partitioned between chloroform and water. The chloroform solution was separated off and washed with brine (x1). The chloroform solution was then dried over anhydrous magnesium sulphate and the solvent rotary evaporated off to give a colouriess gum, 1.94 g. This material was pure enough to be used in the next reaction without any further purification.

$^1$H NMR (270 MHz, $CDCl_3$, δ): 1.04 (s, 9H, $^tBu$), 1.9 (m, 2H, $CH_2C\underline{H}_2CH_2$), 2.01 (s, 3H —$O_2CCH_3$), 2.74 (m, 6H, $C\underline{H}_2N$), 3.7 (m, 2H, $C\underline{H}_2OSi$), 3.8 (s, 6H, DMT-$OC\underline{H}_3$), 4.1 (m,4, $C\underline{H}_2O$), 4.63 (s, 2H, $ArC\underline{H}_2ODMT$), 6.78 (d, 1H, aryl) 6.83 (d, 4H, DMT aryl), 7.2→7.8 (m 20H aryl), 8.05 (d, 2H, aryl)

EXAMPLE 13

Synthesis of N-[acetoxy-2-oxyethyl]-N-[O-(3(O-(4,4'-dimethoxytrityl)-1-oxymethyl)-4-nitrophenyl)-3-oxypropyl]-N-[O-(tert-butyldiphenylsilyl)-3-oxo-6-oxyhexyl] amine (Compound 16, Scheme 4)

To compound 12 (66 mg, 0.10 mmol) dissolved in anhydrous acetonitrile (5 ml) was added potassium carbonate (55 mgs, 0.4 mmol and compound 13a (1 ml of the reaction mixture, approximately 0.30 mmol) and the flask then stoppered with a calcium chloride drying tube. The reaction mixture was then stirred at room temperature for a total of 22 hours after which time the potassium carbonate was filtered off and the solvent removed by rotary evaporation. The resultant oil was then applied to a silica gel column (14 cm×1 cm) and the product eluted off with an ether/pet. ether 40→60° C., 75%/25% mixture. The pure product fractions were combined and evaporated down to a clear gum, 6 mg, 6%, $R_F$ 0.47 in ether/pet. ether 40→60° C., 80%/20%.

$^1$H NMR (270 MHz, $CDCl_3$, δ): 1.05 (s, 9H, $^tBu$), 1.8 (m, 2H, $CH_2C\underline{H}_2CH_2OSi$), 1.9 (m, 5H, $O_2CC\underline{H}_3+ArOC\underline{H}_2$—), 2.76–2.92 (m, 6H, $C\underline{H}_2N$), 3.51 (t, 2H, J=6.6 Hz, $OC\underline{H}_2CH_2CH_2OSi$), 3.79 (s, 6H, DMT-$OCH_3$) 3.85 (m, 2H, $C\underline{H}_2OSi$), 4.12→4.23 (m, 4H, $ArOC\underline{H}_2CH_2+NCH_2C\underline{H}_2OCOCH_3$), 4.64 (s, 2H, $ArC\underline{H}_2ODMT$), 6.83 (m, 5H, 1 aryl+DMT-aryl), 7.23→7.50 (m, 16H, aryl), 7.68 (m, 4H, aryl), 8.10 (d, 1H, J=9.06 Hz, aryl).

By analogues reaction conditions to the above the following compound has also been synthesised utilising the treslate 13b.

N-[acetoxy-2-oxyethyl]-N-[O-(3(O(4,4'-dimethoxytrityl)-1-oxymethyl)-4-nitrophenyl)-3-oxypropyl]-N[O-(tert-butyldiphenylsilyl)-5-methyl-3-oxo-6-oxyhexyl]amine. The compound is a clear gum, $R_F$ 0.53 in ether/pet. ether 40→60° C., 80%/20%.

$^1$H NMR (270 MHz, $CDCl_3$, δ): 0.88 (d, 3H, CH—$C\underline{H}_3$), 1.00 (s, 9H, $^tBu$), 1.9→2.1 (m, 6H, $O_2CCH_3+C\underline{H}$—$CH_3+CH_2C\underline{H}_2CH_2$), 2.7→3.0 (m, 6H, $C\underline{H}_2N$), 3.4→3.7 (m, 4H, $C\underline{H}_2O$—), 3.79 (s, 6H, DMT-$OCH_3$), 4.0→4.4 (m, 6H, $CH_2O$—), 4.64 (s, 2H, Ar $C\underline{H}_2ODMT$), 6.83 (m, 5H, aryl), 7.2→7.7 (m, 20H, aryl), 8.01 (d, 1H, aryl).

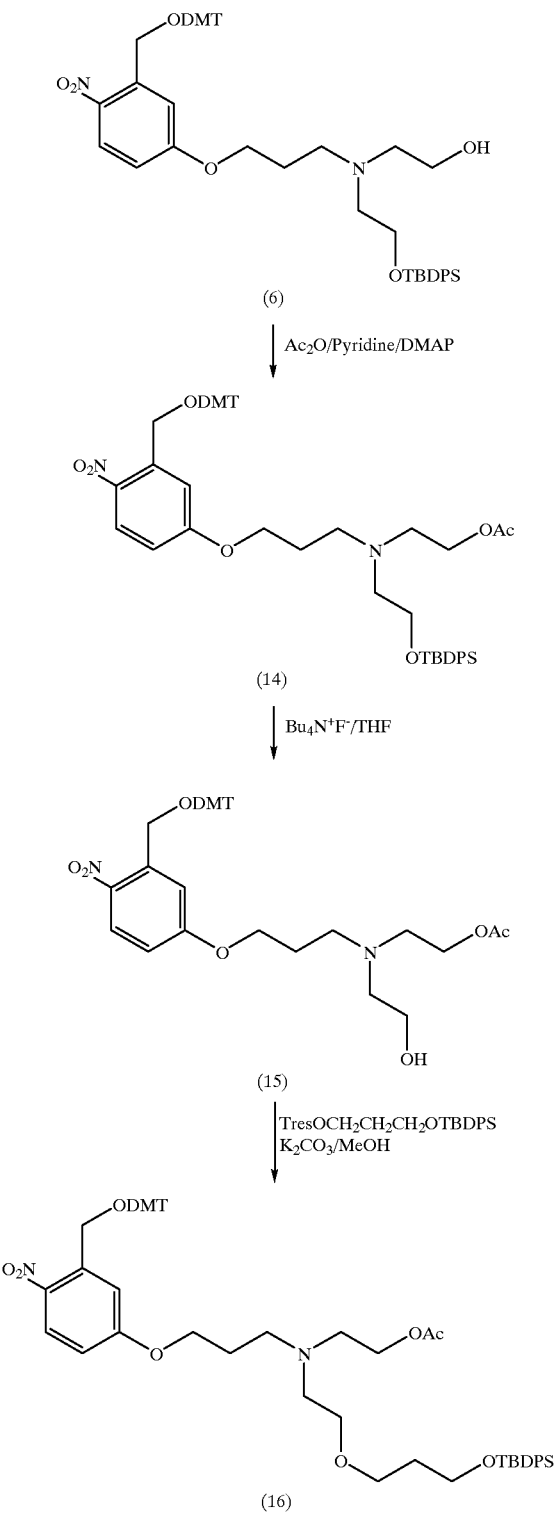

SCHEME 4

(6)

↓ $Ac_2O$/Pyridine/DMAP (14)

↓ $Bu_4N^+F^-$/THF (15)

↓ $TresOCH_2CH_2CH_2OTBDPS$
$K_2CO_3$/MeOH (16)

EXAMPLE 14

Synthesis of Oligonucleotides on Solid Supports

Controlled pore glass carrying linkers 9 and 10 (compounds 9 and 10 in Scheme 2) was loaded into the columns used in the automatic oligonucleotide synthesiser (ABI 381A); the amounts used provided for 0.2 or 1 µmol scale synthesis. The columns were inserted in the automatic synthesiser which was then programmed for appropriate cycles. Two different types of nucleotide precursors were used: normal phosphoramidites, with dimethoxytrityl protecting groups on the 5' hydroxyls; "reverse synthons" with 5' phosphoramidites and dimethoxytrityl protecting groups on the 3' hydroxyls. A list of oligonucleotides synthesised on these supports in shown in Table 4 in which R9 and R10 derive from compounds 9 and 10 respectively. Yields were monitored from the amount of dimethoxytrityl group released at each coupling. These yields corresponded to those obtained on the CPG supports used for conventional oligonucleotide synthesis.

TABLE 4

| End group(s) | Sequence | Normal direction | Reverse direction |
|---|---|---|---|
| R9 | $T_5$ | | √ |
| R10 | $T_5$ | | √ |
| R10, DMT | $T_5$ | | √ |
| R9, DMT | $T_5$ | √ | |
| R10, DMT | $T_5$ | √ | |
| R10 | $A_{10}$ | √ | |

EXAMPLE 15

Synthesis of Tags Under Conditions which Leave the Analyte Intact

After synthesising 5'R9$T_5$ on support 9, the solid support was divided, part was treated with 5 mM tetrabutylammonium fluoride in THF for 10 min. at room temperature to remove the t-butyldiphenylsilyl protecting group. Both samples were treated with 29% ammonia at room temperature overnight to remove the products from the solid support. Ammonia was removed under vacuum, and the solid residue dissolved in water. HPLC showed the successful removal of the silyl protecting group with retention of the DMT group. This example shows that the two protecting groups can be removed under conditions which leave the other in place; and further, that removal of the protecting groups leaves the oligonucleotide chain intact.

EXAMPLE 16

Biochemical Reactions of Tagged Analytes

16a. Enzymatic Phosphorylation of Tagged Oligonucleotides.

For many purposes, it will be useful to have oligonucleotides which have a phosphate group at the 5' end. Such a group is necessary if the oligonucleotide is to be used as the donor in a ligation reaction; and it is a useful way of introducing a radioactive group to test biochemical properties.

The oligonucleotides $A_5$, $A_{10}$, and $T_5$ were made with the tags R9 and R10 attached to the 3' ends, with and without the silyl protecting group removed (This was achieved by treating the oligonucleotide, still on the solid support, with a 5 mM solution of tetrabutylammonium fluoride in acetonitrile, at room temperature for 15 min.) These oligonucleotides were phosphorylated using T4 polynucleotide kinase and gamma-$^{33}$P-ATP using standard protocols recommended by the supplier. Thin layer chromatography of the products on polyethyleneimine (PEI) impregnated cellulose developed in 0.5M ammonium bicarbonate showed in each case that the labelled phosphorus had been transferred almost completely to the oligonucleotide.

16b. Ezymatic Ligation of Tagged Oligonucleotides.

For some applications of tagged oligonucleotides, it will be useful to ligate them to a receptor. We have shown that tagged oligonucleotides can take place in enzymatic ligation by the following tests:
(1) Oligonucleotides tagged at the 5'-end. In this test, the template was 5' ATCAAGTCAGAAAAATATATA (SEQ ID No. 1). This was hybridised to the donor, 3' TAGTTCAGTC (SEQ ID No. 2), which had been phosphorylated at its 5'-end using radioactive phosphorus. Four ligation reactions were carried out, each with a modification of the sequence $T_5$, which could ligate to the 5' phosphorylated end of the donor after hybridising to the run of 5 A's in the template. The four oligoT's used in the reactions differed in the nature of their 5'-end. One had a dimethoxytrityl group attached through the hydroxyl. The second and third had tags R9 and R10 attached to the 5'-end through a phosphodiester bond. The fourth was a positive control, with a normal 5'OH. A negative control lacked any oligoT. Ligation reactions were performed using T4 ligase according to the suppliers instructions. Reactions were analysed by TLC on PEI-cellulose, developed in 0.75M ammonium bicarbonate solution. All four reactions showed an additional spot on the chromatogram, of lower mobility than the donor; as expected, the negative control showed no additional spot. This illustrates how oligonucleotides with different tags can take part in sequence-specific ligation reactions.

Cozzarelli et al (1967) have shown that polynucleotides attached to solid supports can be ligated to an acceptor in the presence of a complementary template.

EXAMPLE 17

Hybridisation of Tagged Oligonucleotides to Oligonucleotides Tethered to a Solid Support.

Example 16b shows that tagged oligonucleotides can take part in ligation reactions, inferring that they can also take part in duplex formation in solution, as ligation depends on this process. The following experiment shows that they can also form duplexes with oligonucleotides tethered to a solid support. $T_{10}$ was synthesised on the surface of a sheet of aminated polypropylene according to the manufacturer's instructions. It is known that this process yields around 10 pmols of oligonucleotide per mm$^2$. A solution in 3.5M tetramethylammonium chloride of $A_{10}$ (65 pmol per microlitre), labelled at the 5'end with $^{33}$P, and tagged at the 3' with R10 was laid on the surface of the derivatised polypropylene and left overnight at 4'. After washing in the hybridisation solvent, it was found that around one third of the probe had hybridised to the tethered oligo-dT. This is close to the theoretical limit of hybridisation, showing that tagged oligonucleotides can take part in hybridisation reactions with high efficiency.

EXAMPLE 18

Photolysis of Tags

The potential to remove tags by photolysis would greatly enhance their usefulness: it would allow for direct analysis by laser desorption in the mass spectrometer; it would provide a simple method of removing the tags to allow other biochemical or chemical processes.
18a. Bulk Photolysis.

The nitrobenzyl group is known to be labile to irradiation at 305 nm. Solutions of R10$A_{10}$ and R10$T_5$ in water were irradiated at 2 cm. from a transilluminator for 20 min. under conditions known to cause no detectable damage to nucleic acids. Analysis by HPLC showed the expected products of photocleavage, with no detectable residue of the original compound.

18b. Laser Induced Photolysis in the Mass Spectrometer.

Samples of $R_{10}T_5$ and $T_5R10$ were deposited on the metal target of a time of flight mass spectrometer (Finnigan Lasermat) without added matrix. The spectrum showed a single saturated peak at around mass 243 in the positive mode that was absent in other samples.

EXAMPLE 19

Identification by mass spectrometry of different tags attached to different analytes.

A sequence of five thymidine residues with a dimethoxytrityl group attached as a tag to the 3'end was synthesised by conventional solid phase methods, but using "reverse synthons". In the mass spectrometer, this compound gave a large and distinct peak at mass 304, in the positive ion mode. By contrast a sequence of ten adenosine residues carrying the tag designated R10 above gave a large and distinct peak at mass 243 in the positive ion mode. In both cases, laser desorption was carried out in the absence of matrix. In both cases the peaks are absent from the oligonucleotides which have no tag. These examples show that it is easily possible to identify an analyte sequence from the presence of a peak in the mass spectrometric trace that derives from a tag incorporated during the synthesis of the analyte, and that characteristic tags are readily identified by their different mass.

FIGURE LEGENDS

FIG. 1. General Scheme for Synthesis of Molecules with Specific Tags.

Synthesis starts from a linker (L) with at least one site for the addition of groups for synthesising the analyte and one for synthesising the tag. (The linker may also be attached reversibly to a solid support during synthesis, and may have sites for generating groups such as charged groups which may help in analysis). $P_a$ and $P_r$ are temporary protecting groups for the analyte precursors and the reporters respectively; they will be removable by different treatments. For example, $P_a$ may be an acid or base labile group such as trityl, F-MOC or t-BOC, and $P_r$ a group removable by treatment with fluoride such as a silyl residue. Groups U–Z may also have protecting groups which must be stable to the reagents used to remove $P_a$ and $P_r$. Coupling chemistries will be different for different analyte types; standard methods are available for oligonucleotide and peptide synthesis.

Three different types of tags are described in FIG. 2. For the first scheme, each extension of the tag is carried out with a reporter which is specific for both position and type of residue added to the analyte. Capping is not important for this scheme.

In the second and third schemes, position is defined by the total mass of reporter reached at the stage in synthesis when the residue is added to the analyte. In this case it is important to terminate part of the extension of the tag by capping a portion of the molecules. The second and third schemes differ from each other in the way the reporters are added. In the second they are in the extension agents; in the third they are in the caps.

FIG. 2. Three Types of Molecule-Specific Tags.

A. Illustrates tags made of reporters (E) that specify both position (subscript) and identity (superscript) of the groups in the analyte (U–Z). Such a set could comprise a series of aliphatic chains of increasing formula weight to specify position: for example, methylene for position 1, ethylene for 2, propylene for 3 etc. These could be differentiated into group-specific types by different isotopic compositions of carbon and hydrogen: for example, there are six different isotopic compositions of $CH_2$, as shown in Table 1 above. Four of these differ by one mass unit and should be readily distinguished by mass spectrometry. Other ways of differential labelling can be envisaged. For example, either position or group could be marked by reporter groups with different charges. Such groups can be separated and recognised by a number of methods including mass spectrometry.

B. Shows tags made by partial synthesis, such that any structure of the analyte is attached to a series of tags; the first member of the series has a reporter group specific for the first group of the analyte; the second has the first reporter plus a second reporter specific for the second group of the analyte and so on. Such a series can readily be made by using two kinds of precursor for extending the tag: one which is protected by a reversible blocking group and one which prevents further extension. For example, a mixture of RX and $P\text{-}(CH_2)_nX$, where R is an non-reactive aliphatic group such as methyl or ethyl, P is a reversible protecting group and X is an activated residue that can react with the group protected by P. Those molecules which have been "capped" by the non-reactive aliphatic group will not take part in the next round of deprotection and extension.

In B the group-specific information is contained in the residues used to extend the synthesis. As in A, the information could be provided using mass isotopes. For example, every addition of a $CH_2$ residue labelled with the isotopes of C and H to $P\text{-}(CH_2)_nX$, adds further sites that can provide different mass to the reporter. The masses of the $(CH_2)_n$ range from 14n to 17n and there are 4+3(n−1) different masses in the range. Thus for the ethylene group there are seven distinct masses in the range 28 to 34, and for the propylene group, ten in the range 42 to 51.

C. Shows how the group-specific information can be added in a different way; in this case it is contained in the chain terminator, the "cap" in example B. Again, different masses could be provided by labelling an aliphatic residue. Positional information is provided by the length of the extension at which the terminator was added. Suppose that E is $(CH_2)_2$—O, and the terminators are isotopically labelled methyl groups with formula weights from 15 to 19. Each extension will add 44 mass units to the reporter. The mass range for the shortest reporter would be from 44+15=59 to 44+19=63. The range for the second position would be from 88+15=103 to 88+19=107, and so on to the sixth where the range is from 284+15=299 to 284+19=303. There is no overlap in this range, and it can be seen that the number of reporters and the range could be extended by using terminators and extensions with more atoms.

LITERATURE CITED

1. Brenner, S. and Lerner, R. A. (1992). Encoded combinatorial chemistry. Proc. Natl. Acad. Sci. USA 89: 5381–5383
2. Drmanac, R., Labat, I., Brukner, I., and Crkvenjakov, R. (1989). Sequencing of megabase plus DNA by hybridization: Theory of the method. Genomics 4: 114–128.
3. Pillai, V. N. R. (1980). Photoremovable protecting groups in organic chemistry. Synthesis 39: 1–26
4. Hoheisel, J. D., Maier, E., Mott, R., McCarthy, L., Grigoriev, A. V., Schalkwyk, L. C., Nitzetic, D., Francis, F. and Lehrach, H. (1993) High resolution cosmid and P1 maps spanning the 14 Mbp genome of the fission yeast *Schizosaccharomyces pombe*. Cell 73: 109–120.
5. Khrapko, K. R., Lysov, Yu. P., Khorlyn, A. A., Shick, V. V., Florentiev, V. L., and Mirzabekov. (1989). An oligonucleotide hybridization approach to DNA sequencing. FEBS Lett. 256: 118–122.
6. Patchornik, A., Amit, B. and Woodward, R. B. (1970). Photosensitive protecting groups. J. AMER. Chem. Soc. 92:21: 6333–6335.
7. Ross, M. T., Hoheisel, J. D., Monaco, A. P., Larin, Z., Zehetner, G., and Lehrach, H. (1992) High density gridded Yac filters; their potential as genome mapping tools. In "Techniques for the analysis of complex genomes." Anand, R. ed. (Academic Press) 137–154.
8. Southern, E. M. (1988). Analyzing Polynucleotide Sequences. International Patent Application PCT GB 89/00460.
9. Southern, E. M., Maskos, U. and Elder, J. K. (1992). Analysis of Nucleic Acid Sequences by Hybridization to Arrays of Oligonucleotides: Evaluation using Experimental Models. Genomics 12: 1008–1017.
10. de Vries, M. S., Elloway, D. J., Wendl, R. H., and Hunziker, H. E. (1992). Photoionisation mass spectrometer with a microscope laser desorption source, Rev. Sci. Instrum. 63(6): 3321–3325.
11. Zubkov, A. M., and Mikhailov, V. G. (1979). Repetitions of s-tuples in a sequence of independent trials. Theory Prob. Appl. 24, 269–282.
12. Cozzarelli, N. R., Melechen, N. E., Jovin, T. M. and Kornberg, A. (1967). BBRC, 28, 578–586.

wherein the analyte moiety has a known predetermined sequence which can be specifically identified by mass spectrometry detection of the tag moiety.

2. The reagent as claimed in claim 1, wherein there is provided a linker group to which is attached the analyte moiety and the tag moiety.

3. The reagent as claimed in claim 1, wherein the analyte moiety is a chain of n analyte residues, and the tag moiety comprises n reporter groups, each reporter group being chosen to identify an analyte residue and its position in the analyte chain, wherein n is at least 2.

4. The reagent as claimed in claim 1, wherein the analyte moiety is linked to the tag moiety by a photocleavable link.

5. The reagent as claimed in claim 1, having a formula A—L—R, where A is a chain of n analyte residues constituting the analyte moiety, L is a linker, R is the tag moiety, and n is 2–20, wherein the tag moiety contains information defining the identity and the location of analyte residues in the analyte moiety.

6. The reagent as claimed in claim 5, wherein R comprises a chain of n reporter groups.

7. The reagent as claimed in claim 2, wherein the linker comprises an aromatic group.

8. The reagent as claimed in claim 7, wherein the linker is joined to the analyte moiety by an ether, amino or thioether bond.

What is claimed is:

1. A reagent comprising
   a) an analyte moiety comprising at least two analyte residues, and linked to
   b) a tag moiety comprising at least two reporter groups suitable for detection by mass spectrometry, excluding oligonucleotides,
   wherein a reporter group identifies an analyte residue, and its position in the analyte moiety, and 9. The reagent as claimed in claim 7, wherein the linker carries an o-nitro group for photocleavage.

10. The reagent as claimed in claim 1, wherein there is present a charged group for analysis by mass spectrometry.

11. The reagent as claimed in claim 1, wherein the tag moiety is cleavable from the rest of the molecule.

12. The reagent as claimed in claim 1, wherein the analyte moiety is an oligonucleotide chain.

13. A library of reagents wherein each reagent comprises:
a) an analyte moiety comprising at least two analyte residues, and linked to
b) a tag moiety comprising at least two reporter groups suitable for detection by mass spectrometry, excluding oligonucleotides,
wherein each reporter group identifies an analyte residue and its position in the analyte moiety,
and wherein the library consists of at least two of the reagents each comprising a different analyte moiety.

14. The library as claimed in claim 13, wherein the different analyte moieties are different oligonucleotides representing complements of known sequences of a predetermined target nucleic acid.

15. The library as claimed in claim 13, wherein the library consists of $4^n$ reagents, each reagent comprising a different analyte moiety which is a different oligonucleotide chain of n nucleotide residues.

16. The library as claimed in claim 13, wherein the reagents are mixed together in solution.

17. An assay method which comprises the steps of:
providing a target substance;
incubating the target substance with one or more reagents, wherein the or each reagent comprises
a) an analyte moiety comprising at least two analyte residues, and linked to
b) a tag moiety comprising at least two reporter groups suitable for detection by mass spectrometry, excluding oligonucleotides,
wherein each reporter group identifies an analyte residue, and its position in the analyte moiety,
and wherein the incubation is conducted under conditions to cause at least one reagent to bind to the target substance;
removing non-bound reagents; and
analyzing recovered tag moieties as an indication of the nature and/or the position of analyte moieties bound to the target substance.

18. The assay method as claimed in claim 17, wherein the target substance is incubated with a library of reagents each of which comprises a different analyte moiety.

19. The assay method as claimed in claim 17, wherein the target substance is an organism or tissue or group of cells.

20. A set of reagents, each reagent comprising:
a) an analyte moiety comprising a chain of n analyte residues, and linked to
b) a tag moiety comprising one or more reporter groups,
wherein a reporter group identifies an analyte residue and its position in the analyte moiety,
wherein, in said set of reagents: a first reagent has a first reporter group which designates a first analyte residue; and an $n^{th}$ reagent has an $n^{th}$ reporter group which designates an $n^{th}$ analyte residue;
wherein n is at least 2; and
wherein the analyte moiety has a known predetermined sequence which can be specifically identified by mass spectrometry detection of the tag moiety.

21. The set of reagents as claimed in claim 20, wherein the reporter groups are suitable for detection by mass spectrometry.

22. The set of reagents as claimed in claim 20, wherein each reagent comprises a linker group to which is attached the analyte moiety and the tag moiety.

23. The set of reagents as claimed in claim 20, wherein in each reagent, the analyte moiety is linked to the tag moiety by a photocleavable link.

24. The set of reagents as claimed in claim 20, wherein each reagent has the formula A—L—R, where A is the chain of n analyte residues constituting the analyte moiety, L is a linker, R is the tag moiety, and n is 2–20, wherein the tag moiety contains information defining the identity and the location of analyte residues in the analyte moiety.

25. The set of reagents as claimed in claim 24, wherein R comprises a chain of up to n reporter groups.

26. The set of reagents as claimed in claim 22, wherein for each reagent, the linker comprises an aromatic group.

27. The set of reagents as claimed in claim 26, wherein the linker is joined to the analyte moiety by an ether, amine or thioether bond.

28. The set of reagents as claimed in claim 26, wherein for each reagent, the linker carries an o-nitro group for photocleavage.

29. The set of reagents as claimed in claim 20, wherein in each reagent, there is present a charged group for analysis by mass spectrometry.

30. The set of reagents as claimed in claim 20, wherein in each reagent, the tag moiety is cleavable from the rest of the molecule.

31. The set of reagents as claimed in claim 20, wherein in each reagent, the analyte moiety is an oligonucleotide chain.

32. A library of at least two sets of reagent, in which each set of reagents comprises a different analyte moiety, wherein in each set of reagents, each reagent comprises:
a) an analyte moiety comprising a chain of n analyte residues, and linked to
b) a tag moiety comprising one or more reporter groups,
wherein a reporter group identifies an analyte residue and its position in the analyte moiety,
and wherein, in each said set of reagents: a first reagent has a first reporter group which designates a first analyte residue; and an $n^{th}$ reagent has an $n^{th}$ reporter group which designates an $n^{th}$ analyte residue;
where n is at least 2.

33. The library as claimed in claim 32, wherein the different analyte moieties are different oligonucleotides representing complements of known sequences of a predetermined target nucleic acid.

34. The library as claimed in claim 32, wherein the library consists of $4^n$ sets of reagents, the reagents of each said set comprising a different analyte moiety which is a different oligonucleotide chain of n nucleotide residues.

35. The library as claimed in claim 32, wherein the reagents are mixed together in solution.

36. An assay method which comprises the steps of:
providing a target substance;
incubating the target substance with one or more sets of reagents, in which the or each set of reagents comprises a different analyte moiety, wherein in the or each set of reagents, each reagent comprises:
a) an analyte moiety comprising a chain of n analyte residues, and linked to
b) a tag moiety comprising one or more reporter groups,
wherein a reporter group identifies an analyte residue and its position in the analyte moiety,
wherein in the or each said set of reagents: a first reagent has a first reporter group which designates a first analyte residue; and an $n^{th}$ reagent has an $n^{th}$ reporter group which designates an $n^{th}$ analyte residue; where n is at least 2;
and wherein the incubation is conducted under conditions to cause at least one set of reagents to bind to the target substance;

removing non-bound reagents; and analyzing recovered tag moieties as an indication of the nature and/or the position of analyte moieties bound to the target substance.

37. The assay method as claimed in claim 36, wherein the target sequence is incubated with a library of a plurality of the sets of reagents.

38. The assay method as claimed in claim 36, wherein the target substance is an organism or tissue or group of cells.

39. A reagent comprising an analyte moiety comprising at least two analyte residues connected via a linkage group to a tag moiety comprising at least one reporter group suitable for detection by mass spectrometry, excluding oligonucleotides, wherein a reporter group identifies an analyte residue and its position in the analyte moiety, and wherein the analyte moiety has a known predetermined sequence which can be specifically identified by mass spectrometry detection of the tag moiety.

40. The reagent as claimed in claim 39, wherein the linkage group is cleavable.

41. The reagent as claimed in claim 40, wherein the linkage group is photocleavable.

42. The reagent as claimed in claim 39, wherein the analyte moiety is a chain of n analyte residues, and a tag moiety comprises up to n reporter groups, each reporter group being chosen to identify an analyte residue and its position in the analyte chain, wherein n is at least 2.

43. The reagent as claimed in claim 39, having a formula A—L—R, where A is a chain of n analyte residues constituting the analyte moiety, L is a linkage group, R is the tag moiety, and n is 2–20, where the tag moiety contains information defining the identity and the location of analyte residues in the analyte moiety.

44. The reagent as claimed in claim 70, wherein the tag moiety R comprises a chain of up to n reporter groups, each reporter group being chosen to identify an analyte residue and its position in the analyte chain.

45. The reagent as claimed in claim 39, wherein the linkage group is joined to the analyte moiety by an ether, amino, or thioether bond.

46. The reagent of claim 45, wherein the linkage group contains an aromatic group.

47. The reagent as claimed in claim 45, wherein the linkage group also carries an o-nitro group for photocleavage.

48. The reagent as claimed in claim 39, wherein there is present a charged group for analysis by mass spectrometry.

49. The reagent as claimed in claim 39, wherein the tag moiety is cleavable from the rest of the molecule.

50. The reagent as claimed in claim 39, wherein the analyte moiety is an oligonucleotide chain.

51. A library of reagents wherein each reagent comprises an analyte moiety comprising at least two analyte residues connected via a linkage group to a tag moiety comprising at least one reporter group suitable for detection by mass spectrometry, excluding oligonucleotides, wherein a reporter group identifies an analyte residue and its position in the analyte moiety, and wherein the library consists of at least two of the reagents each comprising a different analyte moiety.

52. The library as claimed in claim 51, wherein the different analyte moieties are different oligonucleotides representing complements of known sequences of a predetermined target nucleic acid.

53. The library as claimed in claim 51, wherein the reagents are mixed together in solution.

54. An assay method which comprises the steps of:

providing a target substance;

incubating the target substance with one or more reagents, wherein the or each reagent comprises an analyte moiety comprising at least two analyte residues connected via a linkage group to a tag moiety comprising at least one reporter group suitable for detection by mass spectrometry, excluding oligonucleotides, wherein a reporter group identifies an analyte residue and its position in the analyte moiety, and wherein the incubation is conducted under conditions to cause at least one reagent to bind to the target substance;

removing non-bound reagents; and analyzing one or more recovered tag moieties as in indication of the nature and/or position of one or more analyte moieties bound to the target substance.

55. The assay method as claimed in claim 54, wherein the target substance is an organism or tissue or group of cells.

56. The assay method as claimed in claim 54, wherein the target substance is incubated with a library of the said reagents.

* * * * *